(12) United States Patent
Lee et al.

(10) Patent No.: US 7,772,368 B2
(45) Date of Patent: Aug. 10, 2010

(54) DELETION FORMS OF IGE-DEPENDENT HISTAMINE RELEASING FACTOR HAVING HISTAMINE RELEASING ACTIVITY, HRF-BINDING PEPTIDES AND THE USES THEREOF

(75) Inventors: Kyunglim Lee, Seoul (KR); Miyoung Kim, Seoul (KR)

(73) Assignee: Ewha University-Industry Collaboration Foundation, Seoul (KR)

( * ) Notice: Subject to any disclaimer, the term of this patent is extended or adjusted under 35 U.S.C. 154(b) by 377 days.

(21) Appl. No.: 11/307,141

(22) Filed: Jan. 25, 2006

(65) Prior Publication Data

US 2006/0165677 A1    Jul. 27, 2006

(30) Foreign Application Priority Data

Jan. 25, 2005    (KR) .................... 10-2005-0006712

(51) Int. Cl.
   *C07K 1/00*    (2006.01)
(52) U.S. Cl. .................. 530/350; 530/862; 530/868; 424/184.1; 424/185.1; 424/193.1
(58) Field of Classification Search .................. None
   See application file for complete search history.

(56) References Cited

U.S. PATENT DOCUMENTS

| | | | |
|---|---|---|---|
| 6,114,111 | A | 9/2000 | Luo et al. |
| 6,562,576 | B2 | 5/2003 | Manfredi |
| 6,828,112 | B2 | 12/2004 | Manfredi et al. |
| 2002/0094519 | A1 | 7/2002 | McKernan et al. |
| 2002/0106693 | A1 | 8/2002 | Manfredi |
| 2002/0106698 | A1 | 8/2002 | Manfredi |
| 2002/0142348 | A1 | 10/2002 | Georges |
| 2002/0177217 | A1 | 11/2002 | Krieger et al. |
| 2003/0003439 | A1 | 1/2003 | Ostanin |
| 2003/0040012 | A1 | 2/2003 | Kato et al. |
| 2003/0170723 | A1 | 9/2003 | Sato |
| 2003/0172388 | A1 * | 9/2003 | Fujise et al. .................. 800/10 |
| 2003/0211523 | A1 | 11/2003 | Zhang et al. |
| 2004/0146931 | A1 | 7/2004 | Joung et al. |
| 2004/0157279 | A1 | 8/2004 | Nollau et al. |
| 2005/0106636 | A1 | 5/2005 | Stagljar et al. |
| 2005/0176005 | A1 | 8/2005 | Spear |
| 2005/0221280 | A1 | 10/2005 | Westwick et al. |

FOREIGN PATENT DOCUMENTS

| | | |
|---|---|---|
| EP | 0 261 616 A2 | 3/1988 |
| EP | 1 003 853 B1 | 3/1999 |
| EP | 1 098 967 B1 | 2/2000 |
| EP | 1 224 324 B1 | 3/2001 |
| EP | 1 184 463 A1 | 9/2001 |
| KR | 10 2001 0109481 A | 12/2001 |
| KR | 10 2002 0088879 A | 11/2002 |
| WO | WO 92/13965 A1 | 8/1992 |
| WO | WO 2005/105994 A1 | 11/2005 |

OTHER PUBLICATIONS

Budde et al., Clin Exp Allergy, 2003, 33:1175-1182.*
Yoon et al., Archives of Biochemistry and Biophysics, 2000, 384:379-382.*

* cited by examiner

*Primary Examiner*—Michael Szperka
(74) *Attorney, Agent, or Firm*—JHK Law; Joseph Hyosuk Kim

(57) ABSTRACT

The present invention relates to IgE-dependent histamine releasing factor (HRF) and HRF-binding peptides, more precisely, deletion forms of HRF which are able to be formed as dimers containing amino acid sequence represented by SEQ ID NO:3, genes encoding thereof and novel HRF-binding peptides having an activity of inhibiting HRF. The deletion forms of HRF which are able to be formed as dimers of the present invention induces intracellular secretion of histamine and IL-8, making an excellent candidate for a drug for inhibiting allergic reaction triggered by HRF and a kit for detecting HRF in serum of an allergy patient. In addition, novel HFR-binding peptides of the present invention bind to HRF to inhibit the actions of HFR, so they can be effectively used for the prevention and the treatment of allergic diseases of animals including asthma and rhinitis or malaria.

9 Claims, 15 Drawing Sheets pRSET A, B, and C

Comments for pRSET A
2897 nucleotides

T7 promoter: bases 20-39
6xHis tag: bases 112-129
T7 gene 10 leader: bases 133-162
Xpress™ epitope: bases 169-192
Multiple cloning site: bases 202-248
T7 reverse priming site: bases 295-314
T7 transcription terminator: bases 256-385
f1 origin: bases 456-911
bla promoter: bases 943-1047
Ampicillin (bla) resistance gene (ORF): bases 1042-1902
pUC origin: bases 916-2852 (C)

Fig 4.

Multiple Cloning
Site of pRSET A

```
         T7 promoter                                                                    RBS
 21  AATACGACTC ACTATAGGGA GACCACAACG GTTTCCCTCT AGAAATAATT TTGTTTAACT TTAAGAAGGA Polyhistidine (6xHis) region
 91  GATATACAT ATG CGG GGT TCT CAT CAT CAT CAT CAT CAT GGT ATG GCT AGC ATG ACT
               Met Arg Gly Ser His His His His His His Gly Met Ala Ser Met Thr T7 gene 10 leader                  Xpress™ Epitope                  BamH I
148  GGT GGA CAG CAA ATG GGT CGG GAT CTG TAC GAC GAT GAC GAT AAG GAT CGA TGG GGA
     Gly Gly Gln Gln Met Gly Arg Asp Leu Tyr Asp Asp Asp Asp Lys Asp Arg Trp Gly
                                            EK recognition site   EK cleavage site Xho I Sac I Bgl II   Pst I Pvu II  Kpn I Nco I  EcoR I BstB I Hind III
205  TCC GAG CTC GAG ATC TGC AGC TGG TAC CAT GGA ATT CGA AGC TTG ATC GGC CTG CTA
     Ser Glu Leu Glu Ile Cys Ser Trp Tyr His Gly Ile Arg Ser Leu Ile Arg Leu Leu T7 reverse priming site
262  ACA AAG CCC GAA AGG AAG CTG AGT TGG CTG CTG CCA CCG CTG AGC AAT AAC TAG CAT   SEQ ID NO: 38
     Thr Lys Pro Glu Arg Lys Leu Ser Trp Leu Leu Pro Pro Leu Ser Asn Asn ***  His  SEQ ID NO: 39
```

DELETION FORMS OF IGE-DEPENDENT HISTAMINE RELEASING FACTOR HAVING HISTAMINE RELEASING ACTIVITY, HRF-BINDING PEPTIDES AND THE USES THEREOF

TECHNICAL FIELD

The present invention relates to IgE dependent histamine releasing factor (HRF) and HRF-binding peptides, more precisely, deletion forms of HRF which are able to be formed as dimers containing amino acid sequence represented by SEQ ID NO:3, novel HRF-binding peptides inhibiting HRF activity and the uses of the same particularly in the field of medicine.

BACKGROUND ART

It has been generally known that allergic reactions such as asthma, rhinitis, urticaria, anaphylaxis, allergic bronchiectasis, allergy caused by food•drug•pollen•bug, hay fever, cold urticaria, and atopic dermatitis, are attributed to unbalance between cytokine involved in the regulation of IgE (Immunoglobulin E) secretion and IgE (Immunoglobulin E) overexpressed by hypersensitive reaction against allergen (Bachert et al., *Clinical and Experimental Allergy* 28,15-19, 1998; MacDonald and Lichtenstein, *Springer Semin Immunopathol.*, 12, 415-428, 1990).

Once exposed on allergen, immediate reaction occurs, and then cells involved in inflammation are gathered around allergen exposed area by the action of cytokine secreted in mast cells. Few hours later, late-phase reaction (referred as "LPR" hereinafter) occurs owing to various cytokines and histamine secreted from basophils, eosinophils and lymphocytes, and the LPR is progressed in half of allergy patients. Under LPR, histamine is secreted from basophils. And in that case, there is No: allergen causing immediate reaction, so searching for a cause of histamine secretion and progress to LPR has been a major concern. It has been known that histamine is secreted by cytokines such as MCP-3 (Monocyte Chemotatic Protein-3), MCP-1 (Monocyte Chemotatic Protein-1) or RANTES (Regulated upon Activation Normal T-cell Expressed and Secreted), but in fact, only the protein named "HRF" has been proved to secrete histamine in basophils under IgE-dependent LPR (MacDonald et al., *Science,* 269, 688-690,1995). Nevertheless, the mechanism of HRF inducing secretion of histamine in basophils has not been disclosed yet.

HRF is a well-known protein composed of 172 amino acids, and is found in every cytoplasm (Bohm et al., *Biochem. Int.,* 19, 277-286,1989). Among these HRF forming amino acids, 79-123 amino acids form a basic domain, which shows 46% homology with MAP-1B (microtubule-associated protein-1B). Thus, it is presumed that the protein is capable of binding to microtubule. Gachet et al observed under confocal microscope that HRF distribution is consistent with cytoskeleton network distribution, suggesting that HRF is bound to cytoskeleton (Gachet et al., *J. Cell Sci.,* 112,1257-1271, 1999). In the meantime, Sanchez et al reported that HRF is bound to $Ca^{2+}$ although HRF does not belong to calcium binding protein family. It was additionally reported that yeast could survive even when HRF gene was defected in *Saccaromyces cerevisiae* (Sanchez et al., *Electrophoresis,* 18, 150-155, 1997). The reports indicate that HRF belongs to a gene family which has redundant pathway.

HRF is a hydrophilic protein residing in cytoplasm, but has been found in outside of cytoplasm by MacDonald et al. Besides, high level of HRF is detected in serum of a LPR patient, indicating that HRF is extracellular secreted by apoptosis or any other mechanism so as to release histamine through HRF receptors residing on cell membrane (MacDonald et al., *Science,* 269, 688-690, 1995). HRF has known to stimulate IgE-sensitized basophils to secrete histamine, yet concrete IgE mechanism involved in the secretion has not been explained. According to Bheekha-Escura et al, HRF might cause inflammatory reaction in IgE receptor defected cells, suggesting that HRF is not bound directly to IgE but bound to a specific cell membrane receptor (Bheekha-Escura et al., *Blood,* 96, 2191-2198, 2000).

The present inventors have previously reported that i) HRF can pass through cell membrane even though it is a hydrophilic protein, and ii) HRF receptor is confirmed by yeast two-hybrid assay to be the third cytoplasmic domain (CD3) of (Na,K)ATPase (Korean Registered Patent Nos. 457350B1 and 457351B1). The inventors also explained the histamine releasing mechanism of HRF in basophils.

The present inventors found peptide which i) intercepts HRF's passing through the cell and/or ii) intercepts HRF's binding to (Na, K)ATPase to inhibit histamine secretion, and confirmed that such peptide can be useful for the prevention or the treatment of allergic diseases (Korean Registered Patent No. 457350B1).

According to recent report by Budde et al, histamine releasing activity of HRF (HRFmn) isolated from activated monocyte culture supernatant is different from that of recombinant HRF (rHRF), which suggests that HRFmn is not identical factor to rHRF (Budde et al., *Ann. Allergy Asthma Immunol.,* 89, 606-612, 2002). In addition, the report also mentioned that HRF was not detected in HRFmn from human HRF specific ELISA (enzyme-linked immunoabsorbant assay), which suggests that HRFmn has a different structure from rHRF.

Under the judgment that the difference in activity between HRFmn and rHRF is attributed to protease which is massively distributed in allergy patient's blood, the present inventors tried to separate HRF having histamine releasing activity, and as a result, the present inventors found out deletion forms of HRF having better activity than wild type HRF. These deletion forms of HRF, unlike wild type HRF, have intermolecular disulfide bond, by which dimerization is induced and HRF is activated accordingly. The present inventors also prepared novel HRF-binding peptides, and confirmed that the bond of novel HRF-binding peptides to the deletion forms of HRF results in the inhibition of histamine and IL-8 secretion. The present inventors also confirmed that modified HRF binding peptides can be bound to deletion forms of HRF to inhibit histamine and IL-8 releasing activity of HRF, and thus completed this invention by further confirming that deletion forms of HRF and HRF binding peptides can be effectively used for the development of an anti-allergy drug.

DISCLOSURE

Technical Problem

It is an object of the present invention to provide deletion forms of HRF which are able to be formed as dimers which have histamine and IL-8 releasing activity, novel HRF-binding peptides inhibiting HRF and the uses of the same.

SUMMARY OF THE INVENTION

In order to achieve the above object, the present invention provides recombinant deletion forms of IgE-dependent histamine releasing factor (HRF) having enhanced histamine and IL-8 releasing activities by forming dimers with N-terminal deletion in wild type IgE-dependent HRF.

The present invention also provides deletion forms of HRF which are able to be formed as dimers containing amino acid sequence represented by SEQ ID NO:3.

The present invention further provides HRF homo- or hetero-dimers formed between wild type IgE-dependent histamine releasing factors and/or recombinant deletion forms of IgE-dependent histamine releasing factors and a method for preparing the same.

The present invention also provides genes encoding the deletion forms of HRF, a recombinant expression vector harboring the gene, and a transformant transformed with the expression vector.

The present invention also provides histamine and IL-8 releasing inducer containing the deletion forms of HRF as an effective ingredient.

The present invention also provides a method for screening a medicine which inhibits HRF-induced allergy by using the deletion forms of HRF.

The present invention also provides a method for detecting HRF in serum of an allergy patient by using the deletion forms of HRF.

The present invention also provides a novel HRF-binding peptide having the sequence of (V, Y, E or A)-(T, V, F or A)-(Y, P or A)-(P, G or K)-(A, L, S or W)-(A, P or M).

The present invention also provides a pharmaceutical composition for the prevention and the treatment of allergy containing the HRF-binding peptide as an effective ingredient.

The present invention also provides a method for preventing or treating allergy in a mammalian subject comprising administering to the subject a therapeutically effective amount of the HRF-binding peptide of the present invention.

The present invention also provides an allergy diagnostic kit containing the HRF-binding peptide and anti-HRF monoclonal antibody.

The present invention also provides a pharmaceutical composition for the prevention and the treatment of malarial infection comprising the HRF-binding peptide as an effective ingredient.

The present invention also provides a method for preventing or treating malarial infection in a mammalian subject comprising administering to the subject a therapeutically effective amount of the HRF-binding peptide of the present invention.

Further, the present invention provides a method for identification of an HRF-specific receptor using the deletion forms of HRF or the HRF homo- or hetero-dimers of the present invention comprising analysing protein-protein interaction between HRF and the HRF-specific receptor.

Best Modes

Hereinafter, the present invention is described in detail.

The present invention provides recombinant deletion forms of IgE-dependent histamine releasing factor (HRF) having enhanced histamine and IL-8 releasing activities by forming dimers with N-terminal deletion in wild type IgE-dependent HRF.

Deletion forms of HRF of the present invention can easily be synthesized with the sequences provided by the present invention. In addition to the chemical synthesis, deletion forms of HRF of the present invention can also be prepared by recombinant DNA technique using an expression vector having a foreign DNA containing a base sequence encoding the deletion forms of HRF of the invention. The expression vector is designed to reside in vivo and transfect host cells according to a method of Sambrook et al, so as to be expressed in those cells under proper conditions (Sambrook et al., Molecular cloning, 1989, Cold Spring Harbor, Cold Spring Harbor Laboratory Press). Deletion forms of HRF of the present invention can further be prepared by using a fusion protein containing amino acid sequence provided by the present invention.

The amino acid sequences of deletion forms of HRF of the present invention can be modified by the conventional techniques known to those skilled in the art. For example, deletion forms of HRF of the present invention can be modified by adding or reducing the number of amino acids. And deletion forms of HRF can be modified by replacing a specific residue or rearrange the order of residues as long as such modification does not reduce the activity of deletion forms of HRF of the present invention. Not only natural L-α-amino acid but also β, γ, and δ amino acids as well as D-α-amino acid derivatives are available for the modification.

Therefore, it is generally understood to those skilled in the art that deletion forms of HRF of the invention can be modified by the conventional techniques as long as the modification does not change the histamine releasing activity of deletion forms of HRF (neither increase nor decrease), which is completely acceptable for the present invention.

To produce various deletion forms of HRF each having a total-length of rat HRF represented by SEQ ID NO:1 (Accession number U20525, amino acid 1-172), amino acid 11-172 fragment represented by SEQ ID NO:2, amino acid 35-172 fragment represented by SEQ ID NO:3, amino acid 1-112 fragment represented by SEQ ID NO:4, amino acid 39-110 fragment represented by SEQ ID NO:5, amino acid 1-38 fragment represented by SEQ ID NO:6, amino acid 111-172 fragment represented by SEQ ID NO:7, and amino acid 84-108 fragment represented by SEQ ID NO:8, genes encoding the above fragments were isolated from rat HRF total-length sequence (Accession number U20525) represented by SEQ ID NO:9, which were cloned into pRSET-A vector (see FIG. 1-FIG. 4) to transform E. coli. Then, the gene expressed therein was separated and purified.

IL-8 releasing activity in BEAS-2B cells (see FIG. 5) and histamine releasing activity in basophils (see FIG. 6) of each deletion form of HRF were compared according to N-terminal deletion type. As a result, IL-8 releasing activities of 'Del-N11HRF', represented by SEQ ID NO:2, in which 10 amino acid residues in N-terminal of wild type HRF are deleted and 'Del-N35HRF', represented by SEQ ID NO:3, in which 34 amino acid residues in N-terminal of wild type HRF are deleted were greater in BEAS-2B cells than that of wild type HRF. In particular, even under the low level of HRF (1 μg/Ml), which is lower than minimum level of HRF for the secretion of IL-8 in wild type HRF, IL-8 releasing activity was detected. Deletion forms of HRF showed increased histamine releasing activity in IgE sensitized human basophils, compared with wild type HRF.

Therefore, it is concluded that an important part playing a key role in activity of HRF is covered by N-terminal, and thus it is presumed that histamine and IL-8 secretion inducing active HRF is included in LPR allergy patients. The importance of N-terminal of HRF in regulation of HRF functions is also supported by the fact that histamine releasing activity is increased when some of amino acid residues of N-terminal is removed (Del-N11HRF and Del-N35HRF) but is as much as that of wild type HRF when C-terminal is eliminated (Del-C112HRF).

Deletion forms of HRF showed different affinities to the phage expressing HRF specific heptamer peptides. Precisely, wild type HRF and Del-C112HRF showed weak affinities to phage, while Del-N11HRF and Del-N35HRF showed very strong affinities (see FIG. 14). The results are consistent with the difference of activities of each HRF proteins and accordingly was confirmed that there is a limitation in HRF deletion forms to be used for the development of an anti-allergy drug targeting HRF.

Since the active deletion forms of HRF and the mechanisms of them were disclosed by the present invention, it has been understood by those skilled in the art that active HRF can be easily identified from rat, human, rabbit and chicken. So, active HRF forms separated from rat, human, rabbit and chicken can also be included in the scope of the present invention.

The present invention provides a deletion form of HRF which is able to be formed as a dimer containing amino acid sequence represented by SEQ ID NO:3 (Del-N35HRF).

The deletion form of HRF represented by SEQ ID NO:3 has 34 deletions in N-terminal of full-length HRF amino acid sequence of rat (Rattus norvegicus), represented by SEQ ID NO:1, and the deletion form of HRF containing the deleted amino acid sequence has been confirmed to have excellent histamine and IL-8 releasing activity and further the activity is confirmed to be attributed to dimerization by intermolecular disulfide bond.

The present invention further provides HRF homo- or hetero-dimers formed between wild type IgE-dependent histamine releasing factors and/or recombinant deletion forms of IgE-dependent histamine releasing factors and a method for preparing the same.

Thus, based on the assumption that there is a structural difference between deletion forms of HRF and wild type HRF, the present inventors investigated the changes of mobility according to the presence or absence of a reducing agent β-mercaptoethanol (see FIG. 7 and FIG. 8). From non-reducing SDS-PAGE, it was confirmed that deletion forms of HRF showing a high level of activity were observed in dimer site, unlike wild type HRF or C-terminal deleted HRF which show comparatively low levels of activities, indicating that N-terminal deleted deletion forms of HRF have a dimer structure based on intermolecular sulfide bond. HRF contains cysteine at residues 28 and 172, and these amino acids were replaced with serine, resulting in pRSET-A-Del-N11HRF. Another mutation was induced by replacing only the cysteine in residue 172 with serine to produce pRSET-A-Del-N35HRF. The mobility of those mutants was compared in non-reducing SDS-PAGE (see FIG. 9 and FIG. 11). While pRSET-A-Del-N11HRF, pRSET-A-Del-N11HRF-C28S and pRSET-A-Del-N35HRF moved to the dimer position, pRSET-A-Del-N11HRF-C172S and pRSET-A-Del-N35HRF-C172S moved to monomer position, which suggests that cysteine at residue 172 plays an important role in dimerization of HRF.

To investigate the involvement of dimerization of HRF on its activity, IL-8 secretion in BEAS-2B cells of each was measured for comparison (see FIG. 10 and FIG. 12). IL-8 secretion induced by pRSET-A-Del-N11HRF-C172S was 46% of wild type, and IL-8 secretion induced by pRSET-A-Del-N35HRF-C172S was 26% of wild type. The results indicate that cysteine at residue 172 plays a bigger role in activation of HRF than cysteine at residue 28, which is consistent with the result of mobility test in PAGE. The results indicate that the deletion forms of HRF, unlike wild type HRF, exist in the forms of dimer by intermolecular disulfide bond and the structural difference between them is a major cause of difference in activities.

The present inventors examined using a crosslinker whether wild type HRF could form a dimer (FIG. 13). As a result, unlike deletion form of HRF, wild type HRF could hardly form an intermolecular disulfide bond, although wild type HRF could form an intramolecular disulfide bond. This result supports the structural difference between the deletion forms of HRF and wild type HRF and suggests that N-terminal deletion plays a key role in the activation of HRF rather than chemical cross-linking.

Since the failure in dimer formation in wild type HRF is attributed to the absence of intramolecular disulfide bond, there is still a possibility of producing homo-dimers of wild type HRF having improved histamine and IL-8 releasing activities by other methods for in vitro dimerization besides those using dimerization with disulfide bond. Thus, it is clearly understood that the present invention includes homo-dimers of wild type HRF produced by other methods besides those using dimerization with disulfide bond or hetero-dimers formed between deletion forms of HRF in different lengths and wild type HRF, in addition to homo- or hetero-dimers formed between deletion forms of HRF in different lengths.

The method for preparing HRF homo- or hetero-dimers of the present invention is not limited to specific one, and all methods for preparing protein dimers, which have been known to a skilled person in the art, are available. Among these methods, however, the methods described in EP0261616A2, JP1993-032941 A, JP1986-069759, WO05/105994A1 and WO92/013965A1 are preferred. The above patent documents are all incorporated in the present invention as references.

The deletion form of HRF of the present invention forms a dimer by treating a crosslinker after prepared using the sequence provided by the present invention. For example, a dimer is produced by cross-linking sulfur using a crosslinker targeting —SH. The crosslinker comprises 1,4-Di-[3'-(2'pyridyldithio)propionamido]butane (DPDPB), 1,8-Bis-maleimidodiethylene glycol (BM[PEO]2), 1,11-Bis-maleimidotriethylene glycol (BM[PEO]3), Bis-maleimidoethane (BMOE), 1,4-Bis-maleimidobutane (BMB), Bis-maleimidohexane(BMH), 1,6-Hexane-bis-vinylsulfone (HBVS), Dithio-bis-maleimidoethane (DTME) or 1,4-bismaleimidyl-2,3-dihydroxybutane (BMDB).

The present invention also provides an antibody specific for the recombinant deletion form of HRF or the HRF homo- or hetero-dimer of the present invention.

In the present invention, the antibody comprises a polyclonal antibody or a monoclonal antibody. The antibody can be prepared by well-known method in the art.

The present invention also provides genes encoding the deletion forms of HRF.

In the present invention, genes encoding various deletion forms of HRF represented by SEQ ID NO:10-NO:16 were cloned from full-length sequence of rat HRF represented by SEQ ID NO:9 by using the following primer sequences:

Forward primer for cloning of SEQ ID NO:9: CG GGATCC (BamH I) ATG ATT ATC TAC CGG GAC (SEQ ID NO:22);

Reverse primer for cloning of SEQ ID NO:9: CCG CTC-GAG (Xho I) TGT CCT AAG TCC TGG TGT(SEQ ID NO:23);

Forward primer for cloning of SEQ ID NO:10: CG GGATCC (BamH I) GAC GAG CTG TCC TCC GAC AT(SEQ ID NO:24);

Reverse primer for cloning of SEQ ID NO:10: CCC AAGCTT (Hind III) ACA TTT TTC CAT CTC TAA(SEQ ID NO:25);

Forward primer for cloning of SEQ ID NO:11: CG GGATCC (BamH I) AGT GTC AGT AGA ACA GAG(SEQ ID NO:26);

Reverse primer for cloning of SEQ ID NO:11: CCC AAGCTT (Hind III) ACA TTT TTC CAT CTC TAA(SEQ ID NO:27);

Forward primer for cloning of SEQ ID NO:12: TAA-CAAATTGGATCTATCGCCCGCGGAC(SEQ ID NO:28);

Reverse primer for cloning of SEQ ID NO:12: CTTTAC-CCTTTCTGGTTTCTGTTCTTC(SEQ ID NO:29);

Forward primer for cloning of SEQ ID NO:13: CG GGATCC (BamH I) ACA GAG GGT GCC ATC GA(SEQ ID NO:30);

Reverse primer for cloning of SEQ ID NO:13: G AATTC (EcoR I) CCT TTC TGG TTT CTG TT(SEQ ID NO:31);

Forward primer for cloning of SEQ ID NO:14: CG GGATCC (BamH I) ATG ATT ATC TAC CGG GAC(SEQ ID NO:32);

Reverse primer for cloning of SEQ ID NO:14: G AATTC (EcoR I) TCT ACT GAC CAT CTT GC(SEQ ID NO:33);

Forward primer for cloning of SEQ ID NO:15: CG GGATCC (BamH I) GTA AAG CCT TTT ATG ACT(SEQ ID NO:34);

Reverse primer for cloning of SEQ ID NO:15: CCC AAGCTT (Hind III) ACA TTT TTC CAT CTC TAA(SEQ ID NO:35);

Forward primer for cloning of SEQ ID NO:16: CG GGATCC (BamH I) ACA AAA GAG GCC TAC AAA(SEQ ID NO:36); and Reverse primer for cloning of SEQ ID NO:16: CG GGATCC (BamH I) TGG TTT CTG TTC TTC AAG(SEQ ID NO:37).

SEQ ID NO:10 is a nucleotide sequence of a gene encoding a fragment of amino acids 11-172 represented by SEQ ID NO:2;

SEQ ID NO:11 is a nucleotide sequence of a gene encoding a fragment of amino acids 35-172 represented by SEQ ID NO:3;

SEQ ID NO:12 is a nucleotide sequence of a gene encoding a fragment of amino acids 1-112 represented by SEQ ID NO:4;

SEQ ID NO:13 is a nucleotide sequence of a gene encoding a fragment of amino acids 39-110 represented by SEQ ID NO:5;

SEQ ID NO:14 is a nucleotide sequence of a gene encoding a fragment of amino acids 1-38 represented by SEQ ID NO:6;

SEQ ID NO:15 is a nucleotide sequence of a gene encoding a fragment of amino acids 111-172 represented by SEQ ID NO:7; and SEQ ID NO:16 is a nucleotide sequence of a gene encoding a fragment of amino acids 84-108 represented by SEQ ID NO:8.

The nucleotide sequence of a gene encoding a deletion form of HRF of the present invention can be any nucleotide sequence selected from a group consisting of SEQ ID NO:10, NO:11, NO:12, NO:13, NO:14, NO:15 and NO:16. However, it is preferred that the nucleotide sequence includes a sequence represented by SEQ ID NO:11. And nucleotide sequence represented by SEQ ID NO:10 or 11 is more preferred.

The present invention further provides recombinant expression vectors containing genes encoding the deletion forms of HRF of the present invention.

The recombinant expression vectors of the present invention are not limited to specific ones and any recombinant expression vector for the transformation of a microorganism, a plant or an animal can be used as long as it contains a gene encoding a deletion form of HRF.

In the present invention, recombinant vectors pRSET-A-RrHRF, pRSET-A-Del-N11HRF, pRSET-A-Del-N35HRF, pRSET-A-Del-C112HRF, pRSET-A-Del-N39C110HRF, pRSET-A-Del-C38HRF, pRSET-A-Del-N111HRF and pRSET-A-Del-N84C108HRF were constructed by cloning a gene selected from a group consisting of nucleotide sequences each represented by SEQ ID NO:9, NO:10, NO:11, NO:12, NO:13, NO:14, NO:15 and NO:16 into *E coli* expression vector pRSET-A.

The present invention also provides transformants transformed with the above recombinant expression vectors.

The transformants are not limited to specific ones, and *E. coli*, plants or animals can be used herein as long as they can be transfected with the recombinant expression vectors containing genes encoding deletion forms of HRF of the invention.

The present inventors generated transformants by introducing the recombinant expression vectors above into *E. coli* BL21(DE3) or BL21(DE3)pLysS strain. Precisely, BL21 (DE3)-pRSET-A-Del-N11HRF and BL21 (DE3)pLysS-pR-SET-A-Del-N11HRF were constructed by transfecting BL21 (DE3) and BL21 (DE3)pLysS strains with the recombinant expression vector 'pRSET-A-Del-N11HRF'. BL21 (DE3)-pRSET-A-Del-N35HRF and BL21 (DE3)pLysS-pRSET-A-Del-N35HRF were constructed by transfecting BL21 (DE3) and BL21 (DE3)pLysS strains with the recombinant expression vector 'pRSET-A-Del-N35HRF'. In those *E. coli*, T7 RNA polymerase was supposed to be transcribed only under the control of lacUV5 promoter, so when IPTG (isopropyl-β-D-thiogalactopyranoside) was added, T7 RNA polymerase was expressed and deletion forms of HRF were transcribed accordingly. During the purification process, the deficiency of lon protease and omp T outer membrane protease which can decompose protein leads to the mass-production of the deletion forms of HRF.

The present invention also provides a histamine and IL-8 releasing inducer containing the deletion forms of HRF or the HRF homo- or hetero-dimers as an effective ingredient.

The deletion forms of HRF having amino acid sequences each represented by SEQ ID NO:2 and NO:3 showed increased IL-8 releasing activity in BEAS-2B cells, compared with wild type HRF and similarly induced histamine releasing in human basophils. Thus, the deletion forms of HRF can be effectively used as an IL-8 and histamine releasing inducer. The IL-8 and histamine releasing inducer of the present invention can provide an experimental model for the development of an anti-allergy drug. That is, the inducer of the present invention can be effectively used for the development and test of an anti-allergy drug requiring huge amount of allergens.

The present invention also provides a method for screening a drug inhibiting HRF-mediated allergy comprising contacting a drug candidate with the recombinant deletion form of HRF or the HRF homo- or hetero-dimer of the present invention and determining whether the drug candidate binds the recombinant deletion form of HRF or the HRF homo- or hetero-dimer.

The recombinant deletion forms of HRF or the HRF homo- or hetero-dimers of the invention can provide a binding site for HRF-binding peptides, so that they can be used for the development of an anti-allergy drug effective by inhibiting HRF activity. Affinity was investigated by using HBP2 peptide (Korean Registered Patent No: 457350). As a result, deletion forms of HRF having amino acid sequences each represented by SEQ ID NO:5 and NO:8 were proved to have excellent affinities to the peptide (see FIG. 9). Therefore, HRF peptide having the amino acid sequence can be used for detecting a substance of a compound binding to HRF peptide, making the substance and the compound as a useful candidate for an anti-allergy drug.

The recombinant deletion forms of HRF are isolated from cells transfected with recombinant vectors containing genes encoding the deletion forms of HRF by competitive binding assay, which will be reacted with test drugs and other factors known to interact with deletion forms of HRF [for example, HRF-binding peptide (Korean Registered Patent No. 457350B1)]. Among those test drugs, a drug reducing interaction between deletion forms of HRF and HRF-binding peptide is selected. At last, a drug which has a similar structure to HRF-binding peptide and inhibits HRF-induced histamine secretion in cells is screened.

The present invention also provides a method for detecting HRF in serum of a patient comprising preparing serum from the patient; detecting level of HRF by an immunoassay using the recombinant deletion form of HRF or the HRF homo- or heterodimer of the present invention and an antibody thereof.

The antibody comprises a polyclonal antibody or a monoclonal antibody, but the monoclonal antibody is prefered. A monoclonal antibody specific for the recombinant deletion forms of HRF or the HRF homo- or hetero-dimer can be prepared by the conventional art by using the recombinant deletion forms of HRF. The produced antibody specific for the recombinant deletion form of HRF can be included in the scope of the present invention.

A method for detecting HRF in serum of an allergy patient is described in detail hereafter. The HRF-binding peptide or the antibody specific for the deletion form of HRF is coated on bottom, which will be reacted with blood sample. Then, the antibody specific for the deletion form of HRF or the HRF homo- or hetero-dimer or an anti-HRF monoclonal antibody conjugated with a marker [HRP (horse reddish peroxidase), alkaline phosphatase, fluorescein or dye] is added thereto. If the blood sample includes active HRF, it will be colored or fluorescent, indicating that the patient has a potential for allergic disease even without an allergen.

The present invention also provides a novel HRF-binding peptide inhibiting histamine releasing by binding to HRF with high affinity.

The HRF-binding peptide of the present invention has amino acid sequence of (V, Y, E or A)-(T, V, F or A)-(Y, P or A)-(P, G or K)-(A, L, S or W)-(A, P or M), and preferably has the sequence of YVYPSM represented by SEQ ID NO:17.

The HRF-binding peptide of the present invention can be modified by replacing some of residues or rearranging the order of the residues except some residues which are directly involved in the binding or should be reserved, as long as the activity of the peptide does not decrease. Not only natural L-α-amino acid but also β, γ, and δ amino acids as well as D-α-amino acid derivatives are available for the modification.

The effect of electrostatic force or affinity on the binding was investigated by using a peptide in which at least one of amino acid was replaced. As a result, it was typical that binding capacity was sensitively changed when amino acids with either positive charge (Ex: Lys, Arg) or negative charge (Ex: Glu) were replaced. The numbers or the forms of residues to be added or replaced depend on the space required for binding and functions such as hydrophilicity or hydrophobicity. The affinity of a peptide of the present invention to a target protein can be increased by such replacement.

The replacement of residues might cause important changes in functions of the peptide of the invention. According to chosen residue, characteristic changes (electrogram or hydrophobicity of a molecule) and structural changes (side chain or helical structure) occur. In general, major changes in peptide properties are observed when hydrophilic residue such as serine is replaced with hydrophobic residue such as leucine, isoleucine, phenylalanine, valine or alanine, or when residue with positive charge such as lysine, arginine or histidine is replaced with residue with negative charge such as glutamic acid or aspartic acid, or when amino acid without a side chain structure like glycine is replaced with residue with a big side chain.

It will be appreciated that those skilled in the art, on consideration of this disclosure, may make modifications and improvements within the spirit and scope of the present invention as long as the binding capacity to deletion forms of HRF and histamine releasing activity of the HRF-binding peptide are not reduced.

The present inventors obtained the peptide by phage display library screening and re-confirmed by synthetic peptide. The peptide of the invention can be prepared by chemical synthesis or genetic recombination technique. Domain forming the peptide of the present invention can be prepared from blood protein or a part of it. The peptide of the present invention can also be prepared by recombinant DNA technique using an expression vector harboring a foreign DNA having a nucleotide sequence encoding the peptide. The vector transfects proper host cells and is expressed therein under proper conditions according to the method of Sambrook et al (Molecular Cloning, 1989, Cold Spring Harbor, Cold Spring Harbor Laboratory Press). The peptide of the present invention can be prepared by using a fusion protein containing the amino acid sequence of the present invention.

The present invention also provides a pharmaceutical composition for the prevention and the treatment of allergy or malaria containing the HRF-binding peptide of the invention as an effective ingredient.

The HRF-binding peptide of the invention was confirmed to have histamine or IL-8 releasing activity by binding to HRF (see FIG. 16, FIG. 17 and FIG. 18), so it can be effectively used for the prevention and the treatment of allergy.

In the meantime, HRF has been called translationily controlled tumor protein, and it was disclosed in 1998 by Bhisutthibhan et al. that anti-malaria drug artemisinin was effective by binding to malarian HRF (Bhisutthibhan et al., J. Biol. Chem., 1998, 273(26):16192-8). Accordingly, the HRF-binding peptide of the present invention, which has HRF-binding activity, can also be used for the prevention and the treatment of malarial infection as artemisinin can.

Effective dosage of the HRF-binding peptide of the present invention is 30 μg~1 mg/kg. A composition of the present invention can be directly injected in the form of solution or micelle, or administered in various pharmaceutical formulations. A composition of the present invention can be administered to human parenterally or locally such as intravenous injection, hypodermic injection, endothelial injection, muscular injection, etc. To do so, the peptide of the present invention can be suspended or dissolved in pharmaceutically acceptable carriers, and at this time, a water-soluble carrier is preferred.

The present invention provides a diagnostic kit for allergy comprising the HRF-binding peptide and the antibody specific for the deletion form of HRF or the HRF homo- or hetero-dimer of the present invention.

In the test with the diagnostic kit for allergy containing the HRF-binding peptide and the anti-HRF monoclonal antibody of the present invention, if blood is judged as positive to reaction, there is a potential for allergy development even without an allergen. That is, since HRF is floating in blood of LPR allergy patient, blood test with this kit can judge by detecting HRF in blood whether a patient is LPR or not. In the kit of the present invention, HRF-binding peptide is coated on the bottom, which will be reacted with blood sample. And, an anti-HRF monoclonal antibody conjugated with a marker is added thereto for the detection.

Further, the present invention provides a method for identification of an HRF-specific receptor using the deletion forms of HRF or the HRF homo- or hetero-dimers of the present invention comprising analysing protein-protein interaction between HRF and the HRF-specific receptor. In an embodiment, as an analysis of said protein-protein interaction, conventional known protein-protein interaction analysis methods can be used. Particularly, the analysis methods preferably include a co-purification system, a yeast two-hybrid system or a protein chip system, but are not limited thereto.

In an embodiment of the present invention, said co-purification system comprises i) isolating an HRF-HRF-specific receptor complex; ii) purifying the complex; iii) identifying the HRF-specific receptor from the purified complex.

In a preferred embodiment, step i comprises one dimensional (1D) or two dimensional (2D) gel electrophoresis or a liquid chromatography. In another preferred embodiment, step ii comprises a conventional affinity chromatography selected from a group consisting of an immunoprecipitation (Barrett et al., J. Lab. Clin. Med. 1960, 55:605-15) comprising purifying an endogenous protein complex using antibodies thereof or purifying the same after epitope tagging, a non-immunological affinity chromatography such as a GST-pulldown assay (Magnaghi-Jaulin et al., Nucleic Acids Res., 1996, 24(6):1052-8) and a multi-tag affinity purification method such as a tandem affinity purification (TAP) system (Russell et al., Infect Immun., 1980 29(3):999-1006) which uses at least 2 tags for suppressing nonspecific reactions and enhancing recovery yield and reproducibility.

In another embodiment, step iii comprises a peptide fingerprinting such as a matrix-assisted laser desorption/ionization time-of-flight mass spectrometry (MALDI-TOF MS, Hill et al., Rapid Commun. Mass Spectrom., 1991, 5(9):395-9) or a tandem mass spectrometry (tandem MS) selected from a group consisting of a nanoelectrospray ionization (nanoES)-MS/MS (Shevchenko et al., Proc. Natl. Acad. Sci. USA., 1996, 93(25):14440-5), a nanoLC-MS/MS (Oosterkamp et al., J. Mass Spectrom. 1998, 33(10):976-83) and a LC/LC-MS/MS.

In a preferred embodiment, the method for identification of an HRF-specific receptor of the present invention optionally comprises the following step: iv) determining whether the HRF receptor takes part in a histamine releasing process mediated by HRF in vitro or in vivo actually. In a more preferred embodiment, said step iv comprises all known methods for analysing functions of a protein. Particularly, the step iv can be achieved by cloning a gene encoding the identified HRF receptor; constructing a recombinant expression vector comprising the gene; transfecting a histamine releasing cell line with the expression vector; determining whether level of histamine released increases significantly after treatment of the deletion forms of HRF or the HRF homo- or hetero-dimer of the present invention compared with a control cell line which is transfected with mock vector. Alternatively, the step iv can be achieved by preparing a knock-out animal or a cell line having a genome comprising homozygotic disruption in a gene encoding the identified HRF-specific receptor and determining whether level of histamine released decreases significantly after treatment of the deletion forms of HRF or the HRF homo- or hetero-dimers of the present invention compared with a wild type.

Yeast two hybrid system (Fields S. and Song O., Nature., 1989, 340(6230):245-6) is an analysis system using that it is possible to express a reporter gene through an interaction between two proteins (X and Y) and a reconstruction of the proteins into a transcription factor although said proteins are expressed in separated physically, if genes encoding a DNA binding domain (DBD) and a transcription activation domain (TAD) is isolated with a genetic recombination method respectively; fusion gene constructs are prepared by genes encoding X and Y are cloned into the genes encoding DBD and TAD respectively and then expression of the fusion gene constructs is induced in yeast. The system is useful for a highthroughput analysis of protein-protein interaction, since the system is based on genetic recombination and it is possible to screen protein-protein interaction regardless properties of proteins.

In a preferred embodiment, said reporter gene comprises a gene for color selection encoding an enzyme such as β-galactosidase (LacZ), α-galactosidase (MEL1), β-glucuronidase (gusA), green fluorescent protein (GFP) and glucoamylase or a gene for growth selection encoding an enzyme such as imidazoleglycerol-phosphate dehydratase (HIS3), phosphoribosylaminoimidazole-carboxylase (ADE2), α-aminoadipate reductase (LYS2), β-isopropylmalate dehydrogenase (LEU2) and orotidine-5'-phosphate decarboxylase (URA3).

A protein chip is a biochip used for analysis of an interaction between proteins spotted on a solid support with a microarrayer and other molecules such as a protein, a nucleotide, a carbohydrate, a lipid, a cholesterol or other small compounds. Since BIAcore's sensor chip which can be used for detection of an inter-biomolecular interaction was commercialized in 1990s, development of protein chips was accelerated. Because protein chip technology can be applied in various fields such as a diagnosis of diseases, a study on protein activity, a screening of new drug candidates, an assay for interaction of biomolecules, it is being embossed as a key technology of proteomics. In a preferred embodiment, the method for identification of an HRF-specific receptor of the present invention using a protein chip can be achieved by a detection method such as surface plasmon resonance (SPR) assay, surface enhanced laser desorption/ionization time of flight mass spectrometry (SELDI-TOF), fluorescent analysis and electrochemical analysis.

In an embodiment of the present invention, said the protein chip system comprises 1) applying the deletion form of HRF of claim the deletion form of HRF or the HRF homo- or hetero-dimer of the present invention or on the protein chip whereon various proteins whose functions are known or unknown are spotted; and 2) determining whether a protein-protein interaction occurs with or without the antibody of the deletion forms of HRF or the HRF homo- or hetero-dimer of the present invention.

Besides, various methods for analyzing protein-protein interactions known to a skilled person in the art can be used as a method for identification of an HRF-specific receptor. For example, methods described in EPI 003853B1, EPI 098967B1, EP1184463A1, EP1224324B1, U.S. Pat. Nos. 6,114,111, 6,562,576, 6,828,112, US20020094519A1, US20020106693A1, US20020106698A1, US20020142348A1, US20020177217A1, US20030003439A1, US20030040012A1, US20030170723A1, US20030211523A1, US20040146931A1, US20040157279A1, US20050106636A1, US20050176005A1 or US20050221280A1 can be used for the present invention. The documents are incorporated in the present invention as references.

DESCRIPTION OF DRAWINGS

The application of the preferred embodiments of the present invention is best understood with reference to the accompanying drawings, wherein:

FIG. 4 shows nucleotide sequence corresponding to multiple cloning site (MCS) of PREST-A vector described in FIG. 3 and amino acid sequence corresponding to the coding region of the gene.

Mode for Invention

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of Various Deletion forms of HRF

<1-1> Isolation and Amplification of Gene cDNA of a gene encoding HRF was prepared according to the method described in Korean Registered Patent No. 457350B1 and No. 457351B1. Particularly, total RNA was extracted from skeletal muscle of a rat (*Rattus norvegicus*). cDNA library was constructed by using pJG4-5 vector (Invitrogen, Inc., USA) for yeast 2-hybrid assay. CD3 region was inserted into LexA DNA binding domain of pEG202 vector (Brent, R., and Finley, R. L., Jr. Annu. Rev. Genet. 31: 663-704, 1997) by using α2-subunit of (Na,K)ATPase, which was used as a bait for screening. Reporter gene activated positive clones were selected. Then, sequence analysis was performed by sequencing, restriction enzyme mapping and BLAST search. One of those clones was completely identical to IgE-dependent histamine releasing factor (HRF).

Figure 1:
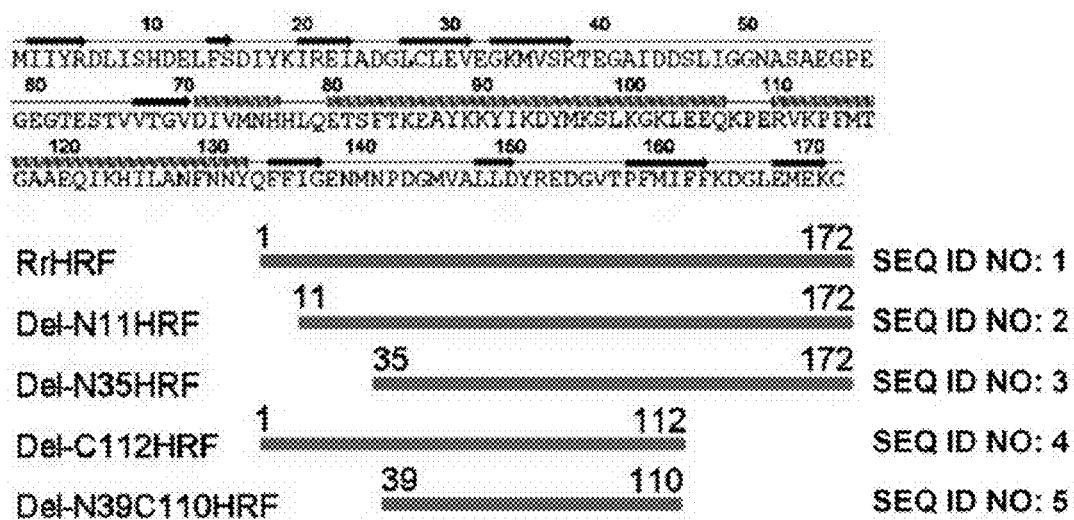
FIG. 1 and FIG. 2 are schematic diagrams showing the various deletion forms of HRF prepared in the present invention.
Figure 2:
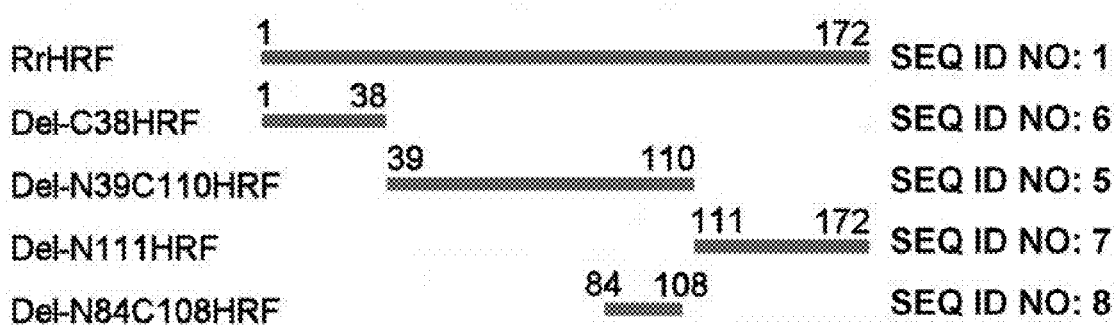

Among rHRF cDNA genes, a gene encoding rat HRF full-length sequence represented by SEQ ID NO:1 (Accession number U20525, amino acids 1-172) is represented by SEQ ID NO:9, a gene encoding fragment of amino acids 11-172 represented by SEQ ID NO:2 is represented by SEQ ID NO:10, a gene encoding fragment of amino acids 35-172 represented by SEQ ID NO:3 is represented by SEQ ID NO:11, a gene encoding fragment of amino acids 1-112 represented by SEQ ID NO:4 is represented by SEQ ID NO:12, a gene encoding fragment of amino acids 39-110 represented by SEQ ID NO:5 is represented by SEQ ID NO:13, a gene encoding fragment of amino acids 1-38 represented by SEQ ID NO:6 is represented by SEQ ID NO:14, a gene encoding fragment of amino acids 111-172 represented by SEQ ID NO:7 is represented by SEQ ID NO:15, a gene encoding fragment of amino acids 84-108 represented by SEQ ID NO:8 is represented by SEQ ID NO:16, and each of those gene was amplified by PCR (FIG. 1 and FIG. 2). All the PCRs were performed as follows; pre-denaturation at 94° C. for 5 minutes, denaturation at 94° C. for 1 minute, annealing at 45-50° C. for 1 minute, elongation at 72° C. for 1 minute, 30 cycles from denaturation to polymerization, and post-elongation at 72° C. for 7 minutes. Primer sequences used for PCR were as mentioned hereinbefore.

<1-2> Construction of Recombinant Expression Vector

Genes each represented by SEQ ID NO:9-NO:16, amplified by PCR in Example <1-1>, were cloned into pRSET-A vector (Invitrogen) respectively to construct recombinant expression vectors, which were named as pRSET-A-RrHRF, pRSET-A-Del-N11HRF, pRSET-A-Del-N35HRF, pRSET-A-Del-C112HRF, pRSET-A-Del-N39C110HRF, pRSET-A-

Figure 3:
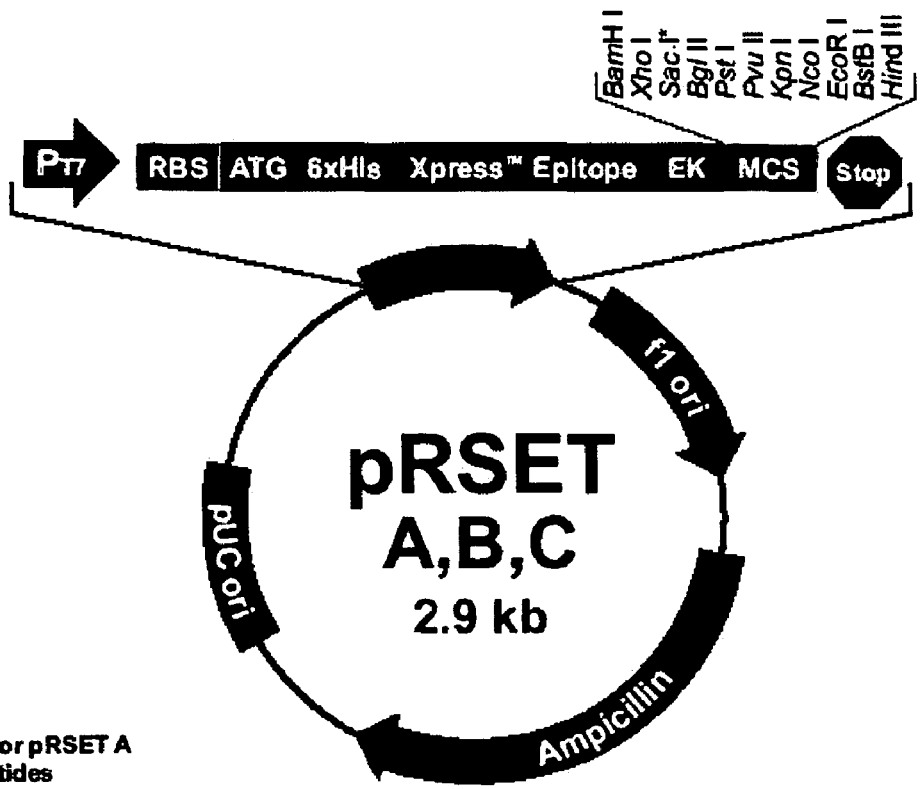
FIG. 3 is a schematic diagram showing the genetic map of pRSET-A vector for the construction of each recombinant deletion form of HRF (pRSET-A-RrHRF, pRSET-A-Del-N11HRF, pRSET-A-Del-N35HRF, pRSET-A-Del-C112HRF, pRSET-A-Del-N39C110HRF, pRSET-A-Del-C38HRF, pRSET-A-Del-N111HRF, pRSET-A-Del-N84C108HRF)

Del-C38HRF, pRSET-A-Del-N111HRF and pRSET-A-Del-N84C108HRF (FIG. 3 and FIG. 4).

<1-3> Preparation of Transformant and Isolation☐ Purification of Deletion Forms of HRF To overexpress each of those deletion forms of HRF, the recombinant expression vectors constructed in Example <1-2> were introduced into *E. coli* BL21(DE3) (Novagen) or BL21 (DE3)pLysS (Novagen).

The *E. coli* transformants were cultured in LB medium containing ampicillin or ampicillin and chloramphnicol, and IPTG (isopropyl β-D-thiogalactoside) was added at the concentration of 0.4 mM when OD reached 0.6. After culturing three more hours, centrifugation was performed at 5,500×g for 5 minutes. The recovered *E. coli* cells were resuspended in binding buffer (5 mM imidazole, 500 mM NaCl, 20 mM Tris-HCl, pH 7.9), followed by ultrasonification. The lysed *E. coli* cells were centrifuged at 39,000×g, and then supernatant was purified by using Ni column (Novagen). Deletion forms of HRF cloned into pRSET-A vector had 6 histidines in N-terminal, so that they could be attached to HIS-binding column charged with Ni. The proteins were extracted by using illusion buffer containing high concentration of imidazole (1 M imidazole, 500 mM NaCl, 20 mM Tris-Hcl, pH 7.9), and salts therein were eliminated by using PD-10 column. The purified deletion forms of HRF were purified again through mono-Q anion exchange column (Amersham Pharmacia Biotech) using NaCl density gradient, which would be used to stimulate BEAS-2B cells (ATCC) and human basophils in following examples.

EXAMPLE 2

IL-8 Releasing Activity in BEAS-2B Cells According to HRF Forms

Figure 5:
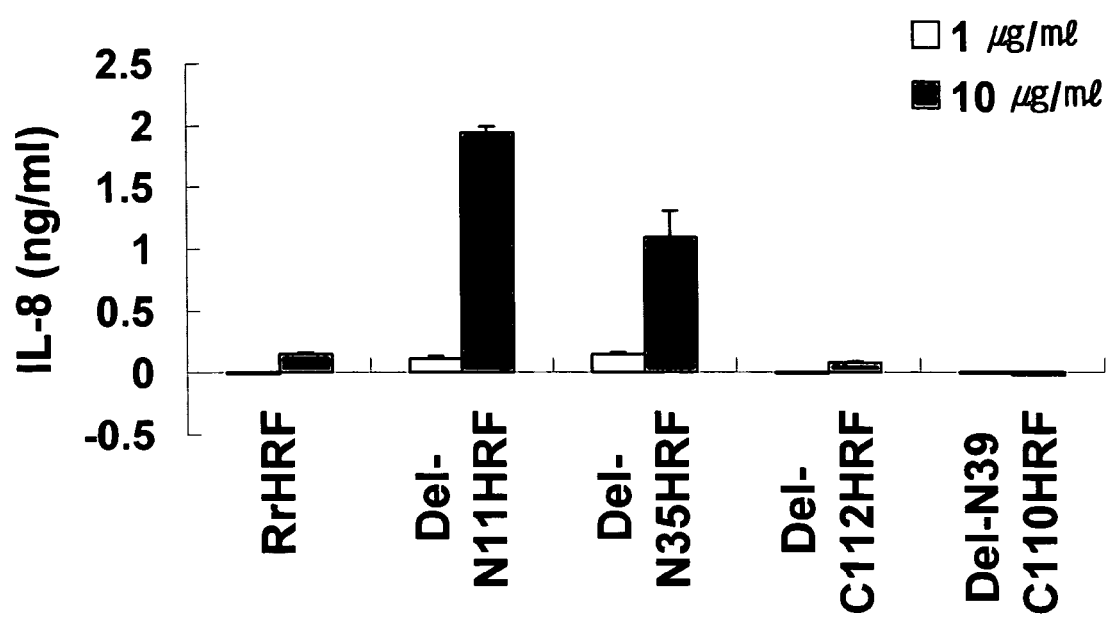
FIG. 5 is a graph showing the comparison of IL-8 secretions in BEAS-2B cells induced by deletion forms of HRF presented in FIG. 1.

The activities of different deletion forms of HRF were compared by investigating IL-8 secretions in BEAS-2B cells (ATCC). BEAS-2B cells were cultured in 48-well plate until they were 70% grown up. Then, the cells were washed with 1% penicillin-streptomycin/BEBM (Clonetics) twice, to which each recombinant protein (RrHRF or each deletion form of HRF) separated in Example <1-3> was added by 1 μg/Ml or 10 μg/Ml. 48 or 24 hours later, supernatant was obtained and IL-8 therein was measured by PIERCE (FIG. 5).

EXAMPLE 3

Histamine Releasing Activity in Human Basophils According to HRF Forms

Figure 6:
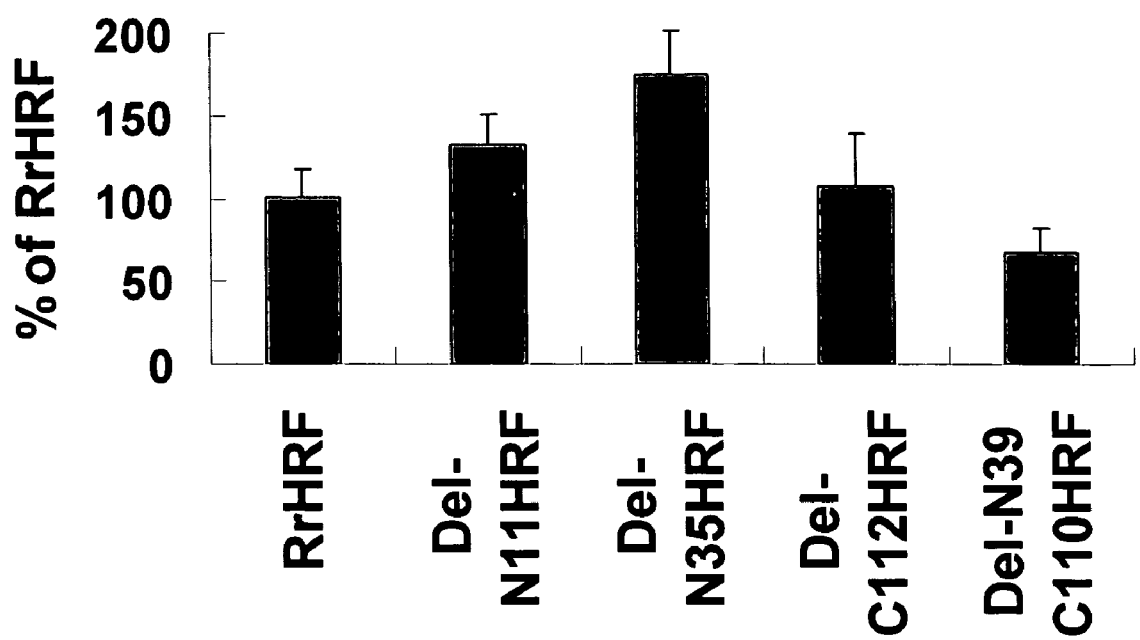
FIG. 6 is a graph showing the comparison of histamine secretions in human basophils in the presence of IgE, which were induced by deletion forms of HRF presented in FIG. 1.

The activities of different deletion forms of HRF were compared by investigating histamine secretions in human basophils. 40 Ml of venous blood was taken from a donor with atopic dermatitis. To the blood sample was added 10 mM of EDTA, an anticoagulant, and 10 Ml of dextran containing 6% saline. The solution stood at room temperature for 90 minutes and then supernatant containing leukocytes was separated, followed by centrifugation at 150×g for 8 minutes. The recovered leukocytes were washed twice with PAG-EDTA (4 mM EDTA, 25 mM PIPES, 110 mM NaCl, 5 mM KCl, 0.003% HSA, 0.1% D-glucose), which were left in cold lactate buffer (13.4 mM lactic acid, 140 mM NaCl, 5 mM KCl, pH 3.9) for 3-5 minutes to eliminate IgE adhered on the surface of cells. The cells were washed with 30 Ml of PAG-EDTA twice and resuspended in PAG-EDTA, followed by IgE-sensitization (1 μg/Ml, Serotec) for 2 hours. Then, the cells were washed with IMDM medium (Gibco BRL) supplemented with 5% FBS twice, to which each recombinant protein (rHRF or each deletion form of HRF) prepared in Example <1-3> was added by 20 μg/Ml. 15 minutes later, human anti-IgE antibody was added thereto. Four hours later, supernatant was obtained. The isolated histamine was measured by histamine analyzer (Astoria Analyzer, Series 300 system) (FIG. 6).

As a result, Del-N11HRF, in which 11 amino acid residues in N-terminal are deleted, represented by SEQ ID NO:2 and Del-N35HRF, in which 35 amino acid residues in N-terminal are deleted, represented by SEQ ID NO:3 have been confirmed to have histamine releasing activities in BEAS-2B cells more effectively than wild type HRF.

EXAMPLE 4

The Effect of Dimerization by Intermolecular Disulfide Bond on HRF Activity

<4-1> Comparison of Mobility by Non-Reducing SDS-PAGE

Figure 7:
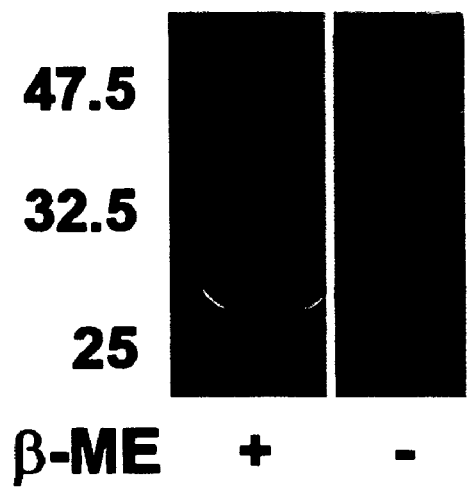
FIG. 7 is a gel electrophoresis photograph showing mobility of RrHRF of FIG. 1 in the presence or absence of a reducing agent.
Figure 8:
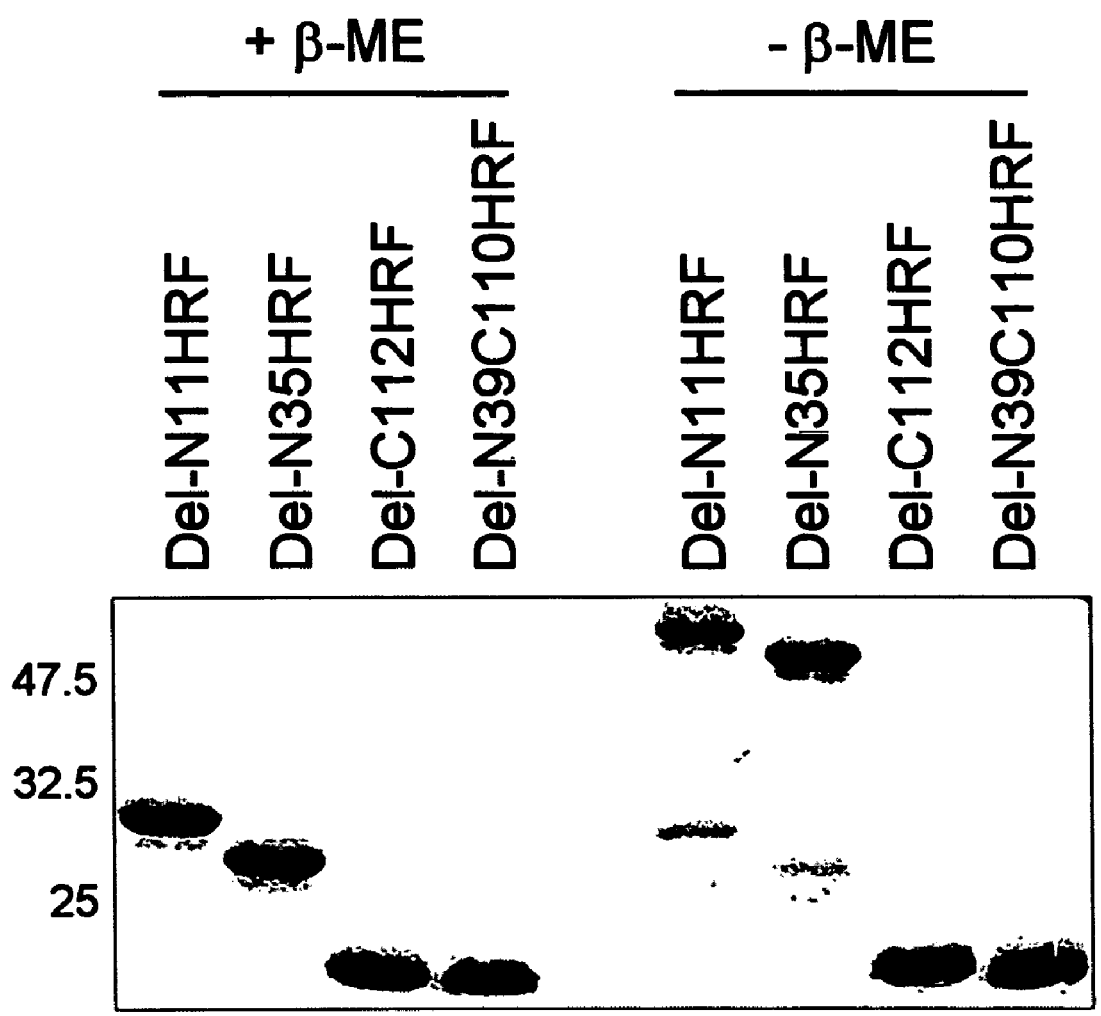
FIG. 8 is a gel electrophoresis photograph showing the difference of mobility of deletion forms of HRF presented in FIG. 1 in the presence or absence of a reducing agent.
Figure 9:
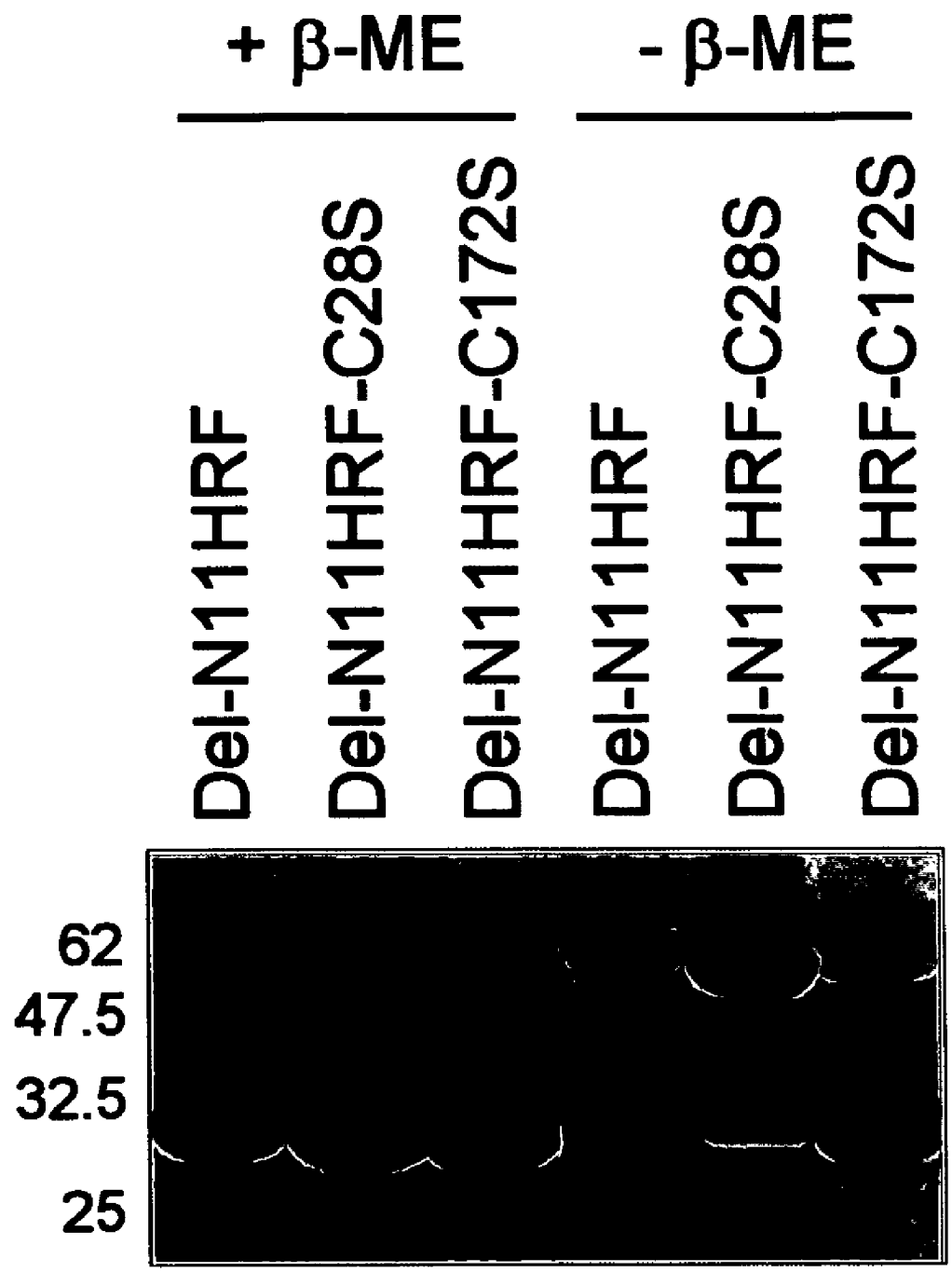
FIG. 9 is a gel electrophoresis photograph showing 'pRSET-A-Del-N11HRF' a recombinant deletion form of HRF and its mutants 'pRSET-A-Del-N11HRF-C28S' and 'pRSET-A-Del-N11HRF-C172S'.
Figure 10:
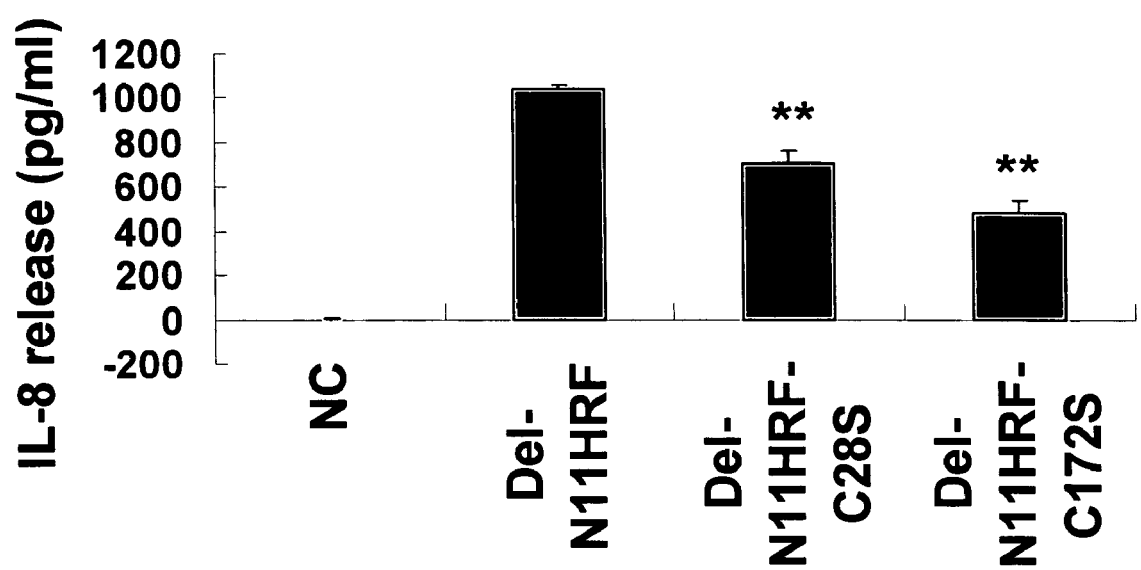
FIG. 10 is a graph showing the comparison of IL-8 secretions in BEAS-2B cells induced by 'pRSET-A-Del-N11HRF' a recombinant deletion form of HRF and its mutants 'pRSET-A-Del-N11HRF-C28S' and 'pRSET-A-Del-N11HRF-C172S'.

Mobility changes according to deletion in N-terminal of each deletion form of HRF prepared in Example <1-3> and wild type HRF were investigated on electrophoresis (FIG. 7 and FIG. 8). SDS-PAGE was performed based on Laemmli's method (Laemmli U.K., Nature, 227, 680-685) with modification. Each protein was mixed with reducing sample buffer [0.125 M Tris-HCl, pH 6.8, 4% (w/v) SDS, 20% (v/v) glycerol, and 2% β-mercaptoethanol (β-ME)] or non-reducing sample buffer, resulting in 15% gel. Proteins having deletions in N-terminals were observed moving toward dimer position, unlike wild type HRF and proteins having deletions in C-terminals. The result indicates that deletion forms of HRF having deletions in N-terminals have different structures from wild type HRF and N-terminal of HRF plays a key role in regulation of HRF functions. In addition, those proteins having deletions in N-terminals have intermolecular disulfide bond.

<4-2> Preparation of a Site-Directed Mutant for the Elimination of Disulfide Bond A mutant was prepared by using site-directed mutagenesis kit (Stratagene) to investigate the HRF activity under the inhibition of the formation of disulfide bond by replacing cysteine residue in N-terminal deletion form of HRF with serine. HRF contains cysteines at $28^{th}$ and $172^{nd}$ residues, so primers CG GAC GGG CTG TCT CTG GAG GTG GA (SEQ ID NO:19) and TC CAC CTC CAG AGA CAG CCC GTC CG (SEQ ID NO:20) were used to construct pRSET-A-Del-N11HRF-C28S. Other primers GAG ATG GAA AAA TCT AAG CTT GAT CCG (SEQ ID NO:21) and CGG ATC AAG CTT AGA TTT TTC CAT CTC (SEQ ID NO:22) were used to construct pRSET-A-Del-N11HRF-C172S and pRSET-A-Del-N35HRF-C172S. PCR amplification was performed using DNA polymerase (Pfu DNA polymerase, Stratagene) as follows; predenaturation of the primer set and template at 95° C. for 5 minutes, denaturation at 95° C. for 1 minute, annealing at 55° C. for 1 minute, polymerization at 68° C. for 7 minutes, 16 cycles from denaturation to polymerization, and final extension at 68° C. for 7 minutes. Dpn I (Stratagene) was added to the PCR product and reacted at 37° C. for 1 hour to digest template DNA selectively. XL1-blue was transfected with the DNA.

Figure 11:
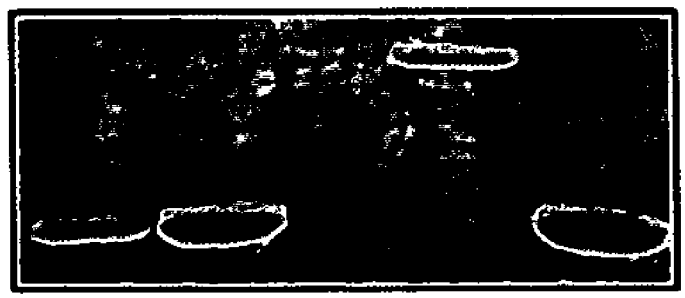
FIG. 11 is a gel electrophoresis photograph showing 'pRSET-A-Del-N35HRF' a recombinant deletion form of HRF and its mutant 'pRSET-A-Del-N35HRF-C172S'.
Figure 12:
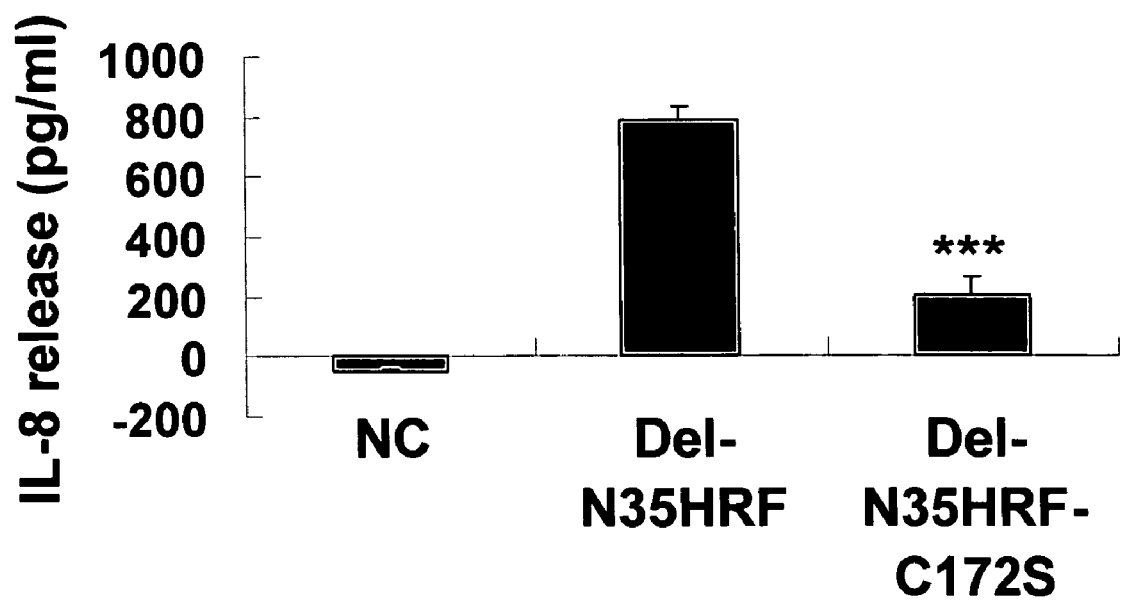
FIG. 12 is a graph showing the comparison of IL-8 secretions in BEAS-2B cells induced by 'pRSET-A-Del-N35HRF' a recombinant deletion form of HRF and its mutant 'pRSET-A-Del-N35HRF-C172S'.

The constructs were examined by DNA sequencing to confirm their being mutated. They were inserted into BL21 (DE3)/pLysS, which were separated and purified by the same manner as described in Example <1-3>. Among those mutants, pRSET-A-Del-N35HRF-C172S was confirmed by non-reducing SDS-PAGE not to form an intermolecular disulfide bond and to have reduced IL-8 releasing activity in BEAS-2B cell line (FIG. 11 and FIG. 12). The results indicate that intermolecular disulfide bond by cysteine at $172^{nd}$ residue plays a key role in activity of N-terminal deletion form of HRF, that is, dimerization is very importantly involved in HRF activity.

<4-3> Cross-Linking of HRF by Chemical Reaction

Figure 13:
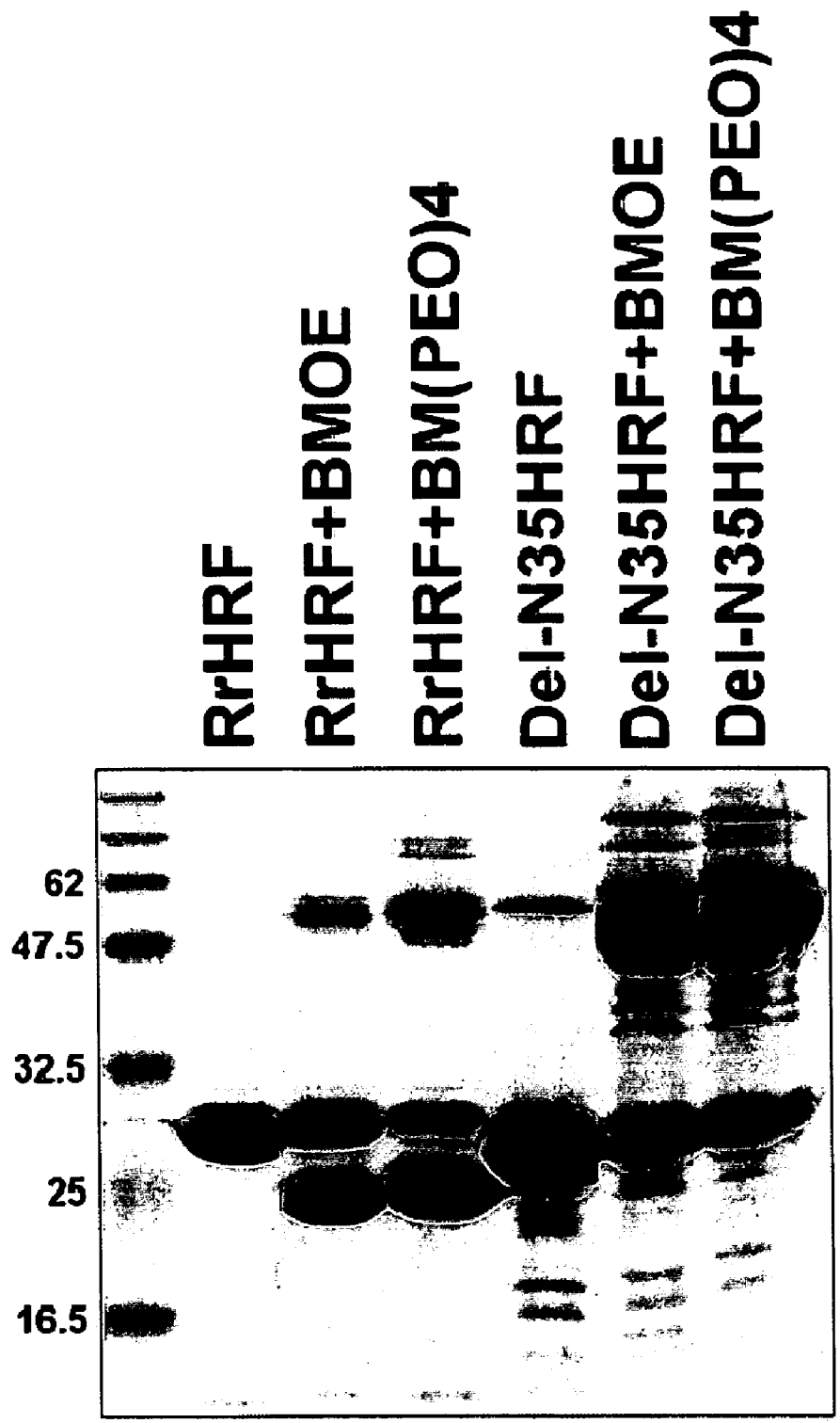
FIG. 13 is a SDS-PAGE photograph showing the dimer forming activities of wild type HRF and deletion forms of HRF.

A crosslinker was used to compare the dimerizations of wild type HRF and deletion form of HRF. Wild type HRF was cross-linked with Del-D35HRF by using —SH targeting crosslinkers, BMOE and BM(PEO)$_3$ (Pierce, USA). To prepare —SH reactable with a crosslinker, Del-N35HRF was treated with 20 mM DTT to reduce intermolecular disulfide bond and then DTT was eliminated using Vivaspin column (Vivascience, USA), followed by changing buffer composition with PBS. Quintuple crosslinkers were treated and each reaction solution stood respectively at 4° C. for 4 hours (treated with BMOE) and at 37° C. for 30 minutes (treated with BM(PEO)$_3$). Over-dose of each crosslinker was eliminated by using Vivaspin column. The resultant protein was quantified, followed by SDS-PAGE (FIG. 13). While reduced Del-N35HRF formed intramolecular disulfide bond by the crosslinker, wild type HRF formed intermolecular disulfide bond, but neither formed a dimer by the crosslinker.

EXAMPLE 5

Phage Display Peptide Clone-Binding Capacities of HRF Forms

Each deletion form of HRF was immobilized on a plastic well, to which phage expressing HRF-binding peptide was added in order to investigate binding capacity of each HRF.

Particularly, each deletion form of HRF dissolved in coating buffer (0.1 M NaHCO$_3$, pH 8.6) at the concentration of 20 μg/Ml was placed on polystyrene microtiter plate by 50 μl, followed by coating at 4° C. for overnight and non-specific binding was blocked with BSA. The plate was washed with 0.1% tween/TBS (TBST) 6 times, to which 30 μl of phage solution diluted in 30 μl of 6% BSA/PBS was added. The solution stood at room temperature for 2 hours. After washing with PBST five times, 100 μl of HRF-conjugated anti-M13 antibody (Pharmacia), diluted in 3% BSA/PBS at the ratio of 1:5000, was added to the solution, followed by standing at room temperature for one hour. After washing 6 times with PBST and once more with PBS, 100 μl of peroxidase substrate solution was added and color development was measured at 405 nm by using ELISA reader (Bio-Rad).

Figure 14:
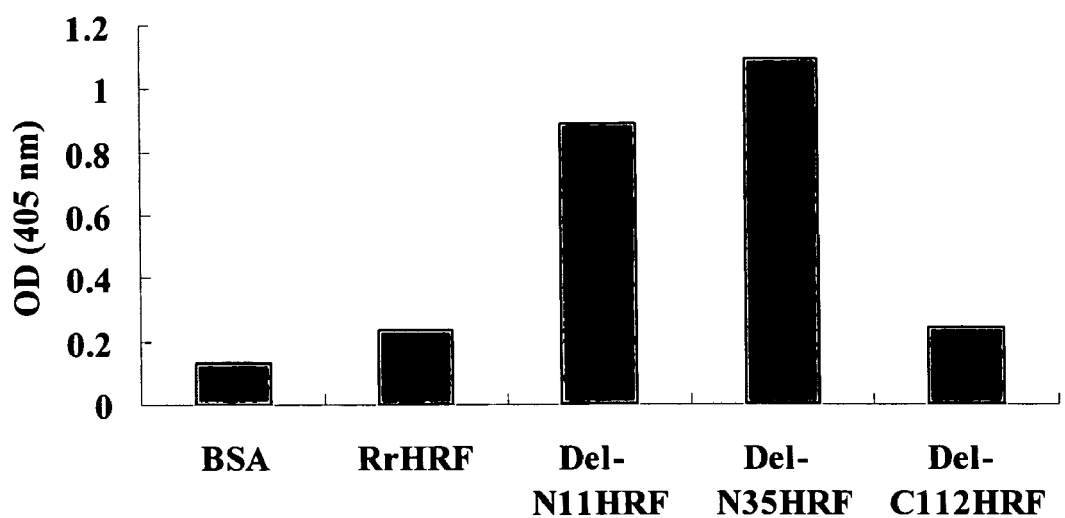
FIG. 14 is a graph showing the affinity of the deletion forms of HRF of FIG. 1 to the phage φ-HBP-2 expressing HRF-binding peptide.

As a result, HRFs showed different affinities to phage expressing HRF-binding heptamer peptide. While RrHRF and Del-C112HRF showed very weak affinities to the phage, Del-N11HRF and Del-N35HRF showed very strong affinities (FIG. 14). These results are consistent with the results of investigation of histamine releasing activity and suggest that usable HRF forms for the development of an anti-allergy drug targeting HRF are limited to some deletion forms of HRF.

Figure 15:
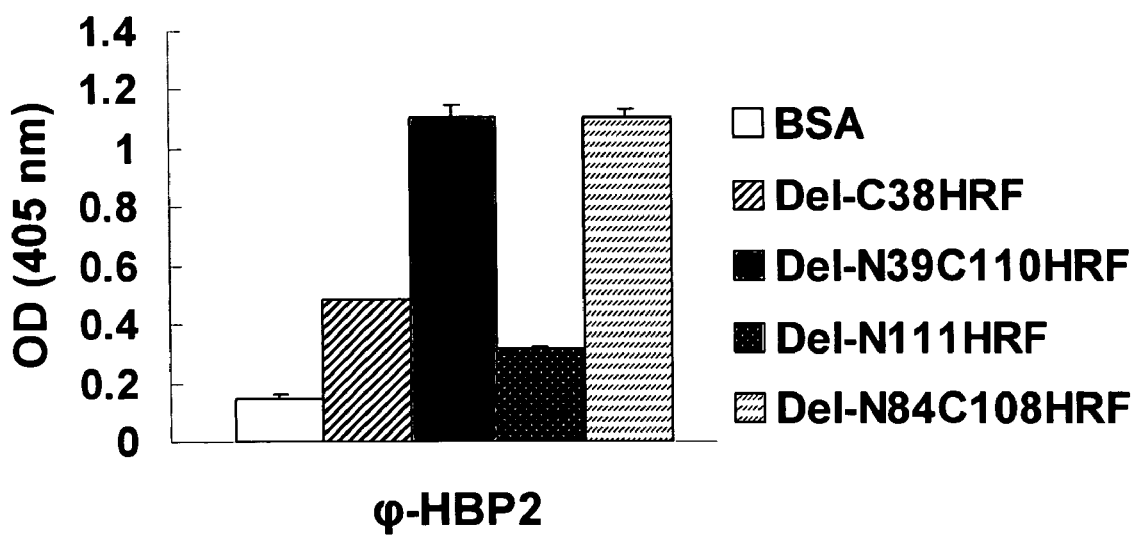
FIG. 15 is a graph showing the affinity of the deletion forms of HRF of FIG. 2 to the phage φ-HBP-2 expressing HRF-binding peptide.

To investigate a binding site to HRF-binding peptide in HRF, HRF was cut into three pieces and affinities to HRF-binding peptide of those pieces were compared. Del-N39C110HRF showed similar level of affinity to that of deletion form of HRF and Del-N84C108HRF, in which more amino acids were deleted, showed high affinity as well (FIG. 15). These results indicate that HRF-binding peptide is adhered to 84-108 region of amino acid of HRF and thus, this region can be useful for screening an anti-allergy drug inhibiting HRF activity.

EXAMPLE 6

Comparison of Activities of HRF-Binding Peptides which can Inhibit the Activities of Deletion Forms of HRF RBL-2H3 cells (ATCC) were cultured in 24-well plate at the concentration of $5 \times 10^4$ cells/well, followed by sensitization with rat IgE antibody (0.2 μg/Ml, Serotec) for 60 minutes. The cells were treated with 1.56 mM of recombinant HRF protein in 5% FBS/MEM medium (positive control). The cells were treated with heptamer peptide (Korean Registered Patent No. 457350B1) with different concentrations (0.0156-15.6 mM). 15 minutes later, rat anti-IgE antibody was added thereto. 4 hours later, supernatant was obtained and the isolated histamine was measured by using histamine analyzer (Astoria Analyzer, Series 300 system).

The interactions between HRF-binding peptides and deletion forms of HRF were investigated in BEAS-2B cells. Del-N35HRF (61 nM) was treated to BEAS-2B cells by the same manner as described in Example 3. At that time, HRF-binding peptide and its mutant in which alanine was replaced (Korean Registered Patent No. 457350B1), and HRF-binding peptides in which amino acid 1 or 7 was deleted were added to Del-N35HRF with different concentrations (6.1-610 nM), followed by standing at room temperature for 10 minutes, which would be added to the cell lines. 24 hours later, supernatant was obtained and the released IL-8 was quantified by PIERCE.

Figure 16:
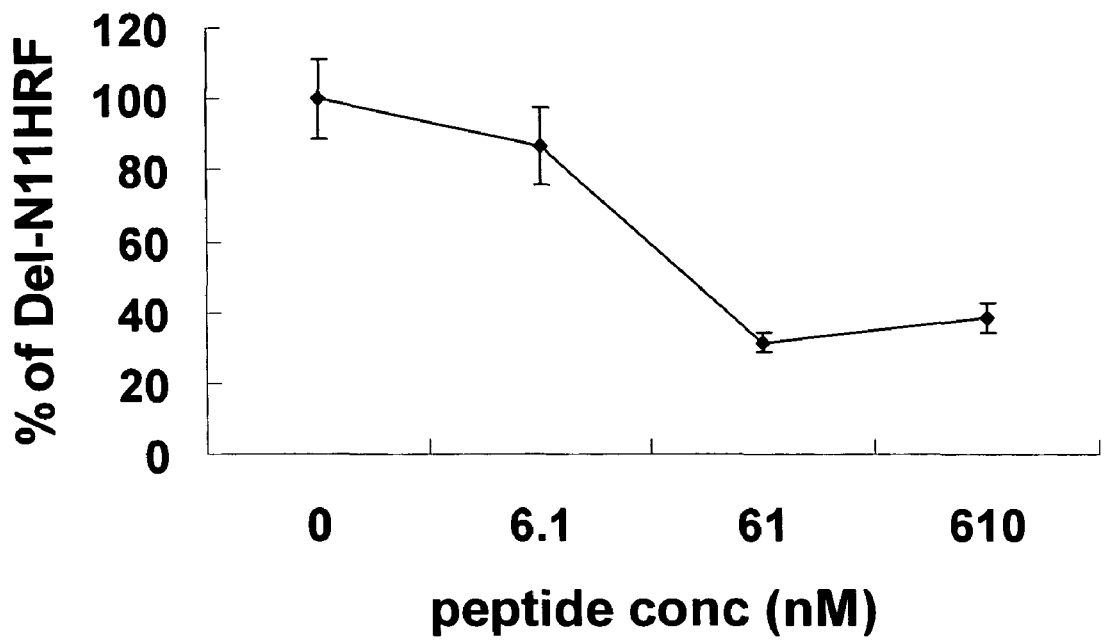
FIG. 16 is a graph showing that an HRF-binding peptide HBP-2 inhibits IL-8 secretion in BEAS-2B cells, which is induced by deletion forms of HRF.
Figure 17:
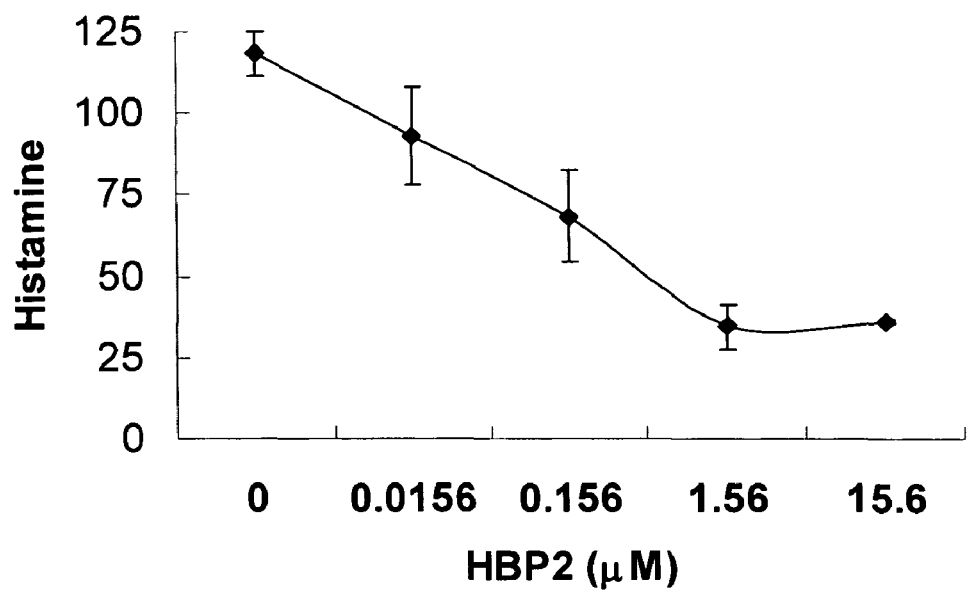
FIG. 17 is a graph showing that an HRF-binding peptide HBP-2 inhibits histamine secretion in RBL-2H3 cells, which is induced by deletion forms of HRF.
Figure 18:
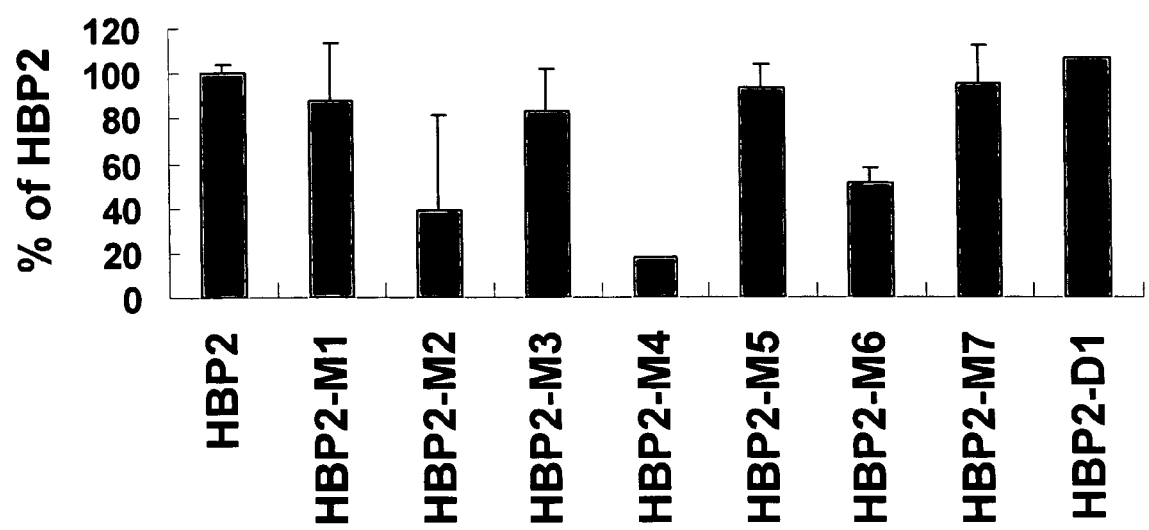
FIG. 18 is a graph showing the comparison of IL-8 secretion inhibition each induced by an HRF-binding peptide HBP-2, its alanine substitutes (HBP2-M1,HBP2-M2, HBP2-M3, HBP2-M4, HBP2-M5, HBP2-M6, HBP2-M7) and 6mer HRF-binding peptide (HBP2-D1) in which $1^{st}$ residue is deleted.

As shown in FIG. 16 and FIG. 17, HRF-binding peptide inhibits histamine releasing by deletion forms of HRF dose-dependently in RBL-2H3 cells, and also inhibits IL-8 secretion by deletion forms of HRF dose-dependently in BEAS-2B cells. HRF-binding peptide having the sequence of WYVYPSM (SEQ ID NO:40) has different activity according to the location of modified amino acids. Precisely, when $2^{nd}$ and $6^{th}$ amino acid residues from N-terminal are replaced with alanine, HRF-binding peptide loses the activity of inhibiting deletion forms of HRF, from which was presumed that serine and tyrosine residues are key factors for the functions of HRF-binding peptides (FIG. 18). The activity of HRF-binding peptide of the present invention represented by SEQ ID NO:17 (HBP2-D1), in which tryptophan residue of N-terminal was deleted, was also investigated. As a result, the HRF-binding peptide showed similar activity to that of original 7-mer peptide, supporting the confirmation that residue 2-residue 6 have the activity of inhibiting active HRF.

INDUSTRIAL APPLICABILITY

As described hereinbefore, deletion forms of HRF which are able to be formed as dimers of the present invention can be effectively used for the development of an anti-allergy drug targeting HRF and for the construction of a kit for detecting HRF in serum of blood sample of an allergy patient by providing active HRF. In addition, deletion forms of HRF of the present invention inhibit IL-8 and histamine releasing in cells, so that they can be effectively used for the development of a preventive or therapeutic agent for malaria and allergic diseases of animals including asthma or rhinitis, etc.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An isolated recombinant dimer consisting of two IgE-dependent histamine releasing factor (HRF), known as translationally controlled tumor protein(TCTP), monomers, wherein said monomers have deletion of amino acids in the N-terminal region, and said dimer has histamine and IL-8 releasing activities, wherein the monomers are joined by covalent bond.

2. The isolated recombinant dimer according to claim 1, wherein the covalent bond is disulfide bond.

3. The isolated recombinant dimer according to claim 1, wherein the HRF is a vertebrate HRF.

4. The isolated recombinant dimer according to claim 1, wherein the deletion comprises the $11^{th}$-$35^{th}$ amino acid residues from the N-terminal of full length HRF of SEQ ID NO:1.

5. The isolated recombinant dimer according to claim 1, wherein at least one of the monomers has the amino acid sequence of SEQ ID NO:2.

6. The isolated recombinant dimer according to claim 1, wherein at least one of the monomers has the amino acid sequence of SEQ ID NO:3.

7. The isolated recombinant dimer according to claim 1, wherein said dimer is a homodimer of two monomers with a deletion of amino acids in the N-terminal region.

8. A histamine releasing inducer comprising the dimer of claim 1 as an effective ingredient.

9. A histamine releasing inducer comprising the dimer of claim 6 as an effective ingredient.

* * * * *

SEQUENCE LISTING

<160> NUMBER OF SEQ ID NOS: 40

<210> SEQ ID NO 1
<211> LENGTH: 172
<212> TYPE: PRT
<213> ORGANISM: Rattus norvegicus

<400> SEQUENCE: 1

Met Ile Ile Tyr Arg Asp Leu Ile Ser His Asp Glu Leu Phe Ser Asp
1               5                   10                  15

Ile Tyr Lys Ile Arg Glu Ile Ala Asp Gly Leu Cys Leu Glu Val Glu
            20                  25                  30

Gly Lys Met Val Ser Arg Thr Glu Gly Ala Ile Asp Asp Ser Leu Ile
        35                  40                  45

Gly Gly Asn Ala Ser Ala Glu Gly Pro Glu Gly Glu Gly Thr Glu Ser
    50                  55                  60

Thr Val Val Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Leu Lys Gly Lys Leu Glu Glu Gln Lys Pro Glu Arg Val Lys
            100                 105                 110

Pro Phe Met Thr Gly Ala Ala Glu Gln Ile Lys His Ile Leu Ala Asn
        115                 120                 125

Phe Asn Asn Tyr Gln Phe Phe Ile Gly Glu Asn Met Asn Pro Asp Gly
    130                 135                 140

Met Val Ala Leu Leu Asp Tyr Arg Glu Asp Gly Val Thr Pro Phe Met
145                 150                 155                 160

Ile Phe Phe Lys Asp Gly Leu Glu Met Glu Lys Cys
                165                 170

<210> SEQ ID NO 2
<211> LENGTH: 162
<212> TYPE: PRT
<213> ORGANISM: Rattus norvegicus

<400> SEQUENCE: 2

Asp Glu Leu Phe Ser Asp Ile Tyr Lys Ile Arg Glu Ile Ala Asp Gly
1               5                   10                  15

Leu Cys Leu Glu Val Glu Gly Lys Met Val Ser Arg Thr Glu Gly Ala
            20                  25                  30

Ile Asp Asp Ser Leu Ile Gly Gly Asn Ala Ser Ala Glu Gly Pro Glu
        35                  40                  45

Gly Glu Gly Thr Glu Ser Thr Val Val Thr Gly Val Asp Ile Val Met
    50                  55                  60

Asn His His Leu Gln Glu Thr Ser Phe Thr Lys Glu Ala Tyr Lys Lys
65                  70                  75                  80

Tyr Ile Lys Asp Tyr Met Lys Ser Leu Lys Gly Lys Leu Glu Glu Gln
                85                  90                  95

Lys Pro Glu Arg Val Lys Pro Phe Met Thr Gly Ala Ala Glu Gln Ile
            100                 105                 110

Lys His Ile Leu Ala Asn Phe Asn Asn Tyr Gln Phe Phe Ile Gly Glu
        115                 120                 125

Asn Met Asn Pro Asp Gly Met Val Ala Leu Leu Asp Tyr Arg Glu Asp
    130                 135                 140

```
Gly Val Thr Pro Phe Met Ile Phe Phe Lys Asp Gly Leu Glu Met Glu
145                 150                 155                 160

Lys Cys
```

<210> SEQ ID NO 3
<211> LENGTH: 138
<212> TYPE: PRT
<213> ORGANISM: Rattus norvegicus

<400> SEQUENCE: 3

```
Met Val Ser Arg Thr Glu Gly Ala Ile Asp Asp Ser Leu Ile Gly Gly
1               5                   10                  15

Asn Ala Ser Ala Glu Gly Pro Glu Gly Glu Gly Thr Glu Ser Thr Val
            20                  25                  30

Val Thr Gly Val Asp Ile Val Met Asn His His Leu Gln Glu Thr Ser
        35                  40                  45

Phe Thr Lys Glu Ala Tyr Lys Lys Tyr Ile Lys Asp Tyr Met Lys Ser
50                  55                  60

Leu Lys Gly Lys Leu Glu Glu Gln Lys Pro Glu Arg Val Lys Pro Phe
65                  70                  75                  80

Met Thr Gly Ala Ala Glu Gln Ile Lys His Ile Leu Ala Asn Phe Asn
                85                  90                  95

Asn Tyr Gln Phe Phe Ile Gly Glu Asn Met Asn Pro Asp Gly Met Val
            100                 105                 110

Ala Leu Leu Asp Tyr Arg Glu Asp Gly Val Thr Pro Phe Met Ile Phe
        115                 120                 125

Phe Lys Asp Gly Leu Glu Met Glu Lys Cys
    130                 135
```

<210> SEQ ID NO 4
<211> LENGTH: 112
<212> TYPE: PRT
<213> ORGANISM: Rattus norvegicus

<400> SEQUENCE: 4

```
Met Ile Ile Tyr Arg Asp Leu Ile Ser His Asp Glu Leu Phe Ser Asp
1               5                   10                  15

Ile Tyr Lys Ile Arg Glu Ile Ala Asp Gly Leu Cys Leu Glu Val Glu
            20                  25                  30

Gly Lys Met Val Ser Arg Thr Glu Gly Ala Ile Asp Asp Ser Leu Ile
        35                  40                  45

Gly Gly Asn Ala Ser Ala Glu Gly Pro Glu Gly Glu Gly Thr Glu Ser
50                  55                  60

Thr Val Val Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Leu Lys Gly Lys Leu Glu Glu Gln Lys Pro Glu Arg Val Lys
            100                 105                 110
```

<210> SEQ ID NO 5
<211> LENGTH: 72
<212> TYPE: PRT
<213> ORGANISM: Rattus norvegicus

<400> SEQUENCE: 5

```
Thr Glu Gly Ala Ile Asp Asp Ser Leu Ile Gly Gly Asn Ala Ser Ala
```

```
              1               5                  10                 15
Glu Gly Pro Glu Gly Glu Gly Thr Glu Ser Thr Val Val Thr Gly Val
              20                 25                 30

Asp Ile Val Met Asn His His Leu Gln Glu Thr Ser Phe Thr Lys Glu
              35                 40                 45

Ala Tyr Lys Lys Tyr Ile Lys Asp Tyr Met Lys Ser Leu Lys Gly Lys
              50                 55                 60

Leu Glu Glu Gln Lys Pro Glu Arg
65                  70

<210> SEQ ID NO 6
<211> LENGTH: 38
<212> TYPE: PRT
<213> ORGANISM: Rattus norvegicus

<400> SEQUENCE: 6

Met Ile Ile Tyr Arg Asp Leu Ile Ser His Asp Glu Leu Phe Ser Asp
1               5                  10                 15

Ile Tyr Lys Ile Arg Glu Ile Ala Asp Gly Leu Cys Leu Glu Val Glu
              20                 25                 30

Gly Lys Met Val Ser Arg
        35

<210> SEQ ID NO 7
<211> LENGTH: 62
<212> TYPE: PRT
<213> ORGANISM: Rattus norvegicus

<400> SEQUENCE: 7

Val Lys Pro Phe Met Thr Gly Ala Ala Glu Gln Ile Lys His Ile Leu
1               5                  10                 15

Ala Asn Phe Asn Asn Tyr Gln Phe Phe Ile Gly Glu Asn Met Asn Pro
              20                 25                 30

Asp Gly Met Val Ala Leu Leu Asp Tyr Arg Glu Asp Gly Val Thr Pro
              35                 40                 45

Phe Met Ile Phe Phe Lys Asp Gly Leu Glu Met Glu Lys Cys
              50                 55                 60

<210> SEQ ID NO 8
<211> LENGTH: 25
<212> TYPE: PRT
<213> ORGANISM: Rattus norvegicus

<400> SEQUENCE: 8

Thr Lys Glu Ala Tyr Lys Lys Tyr Ile Lys Asp Tyr Met Lys Ser Leu
1               5                  10                 15

Lys Gly Lys Leu Glu Glu Gln Lys Pro
              20                 25

<210> SEQ ID NO 9
<211> LENGTH: 519
<212> TYPE: DNA
<213> ORGANISM: Rattus norvegicus

<400> SEQUENCE: 9
atgatcatct accgggacct catcagccat gacgagctgt tctccgacat ctacaagatc     60
cgggagatcg cggacgggct gtgcctggag gtggagggca agatggtcag tagaacagag    120
ggtgccatcg atgattcact cattggtgga aatgcttccg ctgaaggtcc ggagggcgaa    180
```

```
ggtaccgaaa gcacagtagt caccggtgtt gacattgtca tgaaccatca cttacaagaa      240
accagcttca caaaagaggc ctacaaaaag tatatcaaag actacatgaa atcactcaag      300
ggcaaacttg aagaacagaa accagaaagg gtaaagcctt ttatgactgg agctgcagag      360
caaattaagc acatccttgc taatttcaat aactaccagt tttttattgg tgaaaacatg      420
aatccagatg gcatggttgc tctactggac taccgtgaag atggtgtgac tccattcatg      480
attttcttta aggatggctt agagatggaa aaatgttaa                            519

<210> SEQ ID NO 10
<211> LENGTH: 489
<212> TYPE: DNA
<213> ORGANISM: Rattus norvegicus

<400> SEQUENCE: 10
gacgagctgt tctccgacat ctacaagatc cgggagatcg cggacgggct gtgcctggag       60
gtggagggca agatggtcag tagaacagag ggtgccatcg atgattcact cattggtgga     120
aatgcttccg ctgaaggtcc ggagggcgaa ggtaccgaaa gcacagtagt caccggtgtt     180
gacattgtca tgaaccatca cttacaagaa accagcttca caaaagaggc ctacaaaaag     240
tatatcaaag actacatgaa atcactcaag ggcaaacttg aagaacagaa accagaaagg     300
gtaaagcctt ttatgactgg agctgcagag caaattaagc acatccttgc taatttcaat     360
aactaccagt tttttattgg tgaaaacatg aatccagatg gcatggttgc tctactggac     420
taccgtgaag atggtgtgac tccattcatg attttcttta aggatggctt agagatggaa     480
aaatgttaa                                                            489

<210> SEQ ID NO 11
<211> LENGTH: 417
<212> TYPE: DNA
<213> ORGANISM: Rattus norvegicus

<400> SEQUENCE: 11
atggtcagta gaacagaggg tgccatcgat gattcactca ttggtggaaa tgcttccgct       60
gaaggtccgg agggcgaagg taccgaaagc acagtagtca ccggtgttga cattgtcatg     120
aaccatcact tacaagaaac cagcttcaca aaagaggcct acaaaaagta tatcaaagac     180
tacatgaaat cactcaaggg caaacttgaa gaacagaaac cagaaagggt aaagcctttt     240
atgactggag ctgcagagca aattaagcac atccttgcta atttcaataa ctaccagttt     300
tttattggtg aaaacatgaa tccagatggc atggttgctc tactggacta ccgtgaagat     360
ggtgtgactc cattcatgat tttctttaag gatggcttag agatggaaaa atgttaa       417

<210> SEQ ID NO 12
<211> LENGTH: 336
<212> TYPE: DNA
<213> ORGANISM: Rattus norvegicus

<400> SEQUENCE: 12
atgatcatct accgggacct catcagccat gacgagctgt tctccgacat ctacaagatc       60
cgggagatcg cggacgggct gtgcctggag gtggagggca agatggtcag tagaacagag     120
ggtgccatcg atgattcact cattggtgga aatgcttccg ctgaaggtcc ggagggcgaa     180
ggtaccgaaa gcacagtagt caccggtgtt gacattgtca tgaaccatca cttacaagaa     240
accagcttca caaaagaggc ctacaaaaag tatatcaaag actacatgaa atcactcaag     300
ggcaaacttg aagaacagaa accagaaagg gtaaag                              336
```

<210> SEQ ID NO 13
<211> LENGTH: 216
<212> TYPE: DNA
<213> ORGANISM: Rattus norvegicus

<400> SEQUENCE: 13

```
acagagggtg ccatcgatga ttcactcatt ggtggaaatg cttccgctga aggtccggag      60
ggcgaaggta ccgaaagcac agtagtcacc ggtgttgaca ttgtcatgaa ccatcactta     120
caagaaacca gcttcacaaa agaggcctac aaaaagtata tcaaagacta catgaaatca     180
ctcaagggca aacttgaaga acagaaacca gaaagg                               216
```

<210> SEQ ID NO 14
<211> LENGTH: 114
<212> TYPE: DNA
<213> ORGANISM: Rattus norvegicus

<400> SEQUENCE: 14

```
atgatcatct accgggacct catcagccat gacgagctgt tctccgacat ctacaagatc      60
cgggagatcg cggacgggct gtgcctggag gtggagggca agatggtcag taga           114
```

<210> SEQ ID NO 15
<211> LENGTH: 189
<212> TYPE: DNA
<213> ORGANISM: Rattus norvegicus

<400> SEQUENCE: 15

```
gtaaagcctt ttatgactgg agctgcagag caaattaagc acatccttgc taatttcaat      60
aactaccagt tttttattgg tgaaaacatg aatccagatg catggttgc tctactggac     120
taccgtgaag atggtgtgac tccattcatg attttcttta aggatggctt agagatggaa     180
aaatgttaa                                                             189
```

<210> SEQ ID NO 16
<211> LENGTH: 74
<212> TYPE: DNA
<213> ORGANISM: Rattus norvegicus

<400> SEQUENCE: 16

```
caaaagaggc ctacaaaaag tatatcaaag actacatgaa atcactcaag ggcaaacttg      60
aagaacagaa acca                                                        74
```

<210> SEQ ID NO 17
<211> LENGTH: 6
<212> TYPE: PRT
<213> ORGANISM: Artificial Sequence
<220> FEATURE:
<223> OTHER INFORMATION: HBP2-D1

<400> SEQUENCE: 17

Tyr Val Tyr Pro Ser Met
1               5

<210> SEQ ID NO 18
<211> LENGTH: 25
<212> TYPE: DNA
<213> ORGANISM: Artificial Sequence
<220> FEATURE:
<223> OTHER INFORMATION: primer for C28s mutation

<400> SEQUENCE: 18
cggacgggct gtctctggag gtgga                                         25

<210> SEQ ID NO 19
<211> LENGTH: 25
<212> TYPE: DNA
<213> ORGANISM: Artificial Sequence
<220> FEATURE:
<223> OTHER INFORMATION: primer for C28s mutation

<400> SEQUENCE: 19
tccacctcca gagacagccc gtccg                                         25

<210> SEQ ID NO 20
<211> LENGTH: 27
<212> TYPE: DNA
<213> ORGANISM: Artificial Sequence
<220> FEATURE:
<223> OTHER INFORMATION: primer for C172s mutation

<400> SEQUENCE: 20
gagatggaaa aatctaagct tgatccg                                       27

<210> SEQ ID NO 21
<211> LENGTH: 27
<212> TYPE: DNA
<213> ORGANISM: Artificial Sequence
<220> FEATURE:
<223> OTHER INFORMATION: primer for C172S mutaion

<400> SEQUENCE: 21
cggatcaagc ttagattttt ccatctc                                       27

<210> SEQ ID NO 22
<211> LENGTH: 26
<212> TYPE: DNA
<213> ORGANISM: Artificial Sequence
<220> FEATURE:
<223> OTHER INFORMATION: primer for sequence number 9

<400> SEQUENCE: 22
cgggatccat gattatctac cgggac                                        26

<210> SEQ ID NO 23
<211> LENGTH: 27
<212> TYPE: DNA
<213> ORGANISM: Artificial Sequence
<220> FEATURE:
<223> OTHER INFORMATION: primer for sequence number 9

<400> SEQUENCE: 23
ccgctcgagt gtcctaagtc ctggtgt                                       27

<210> SEQ ID NO 24
<211> LENGTH: 28
<212> TYPE: DNA
<213> ORGANISM: Artificial Sequence
<220> FEATURE:
<223> OTHER INFORMATION: primer for sequence number 10

<400> SEQUENCE: 24
cgggatccga cgagctgtcc tccgacat                                      28

<210> SEQ ID NO 25
<211> LENGTH: 27
<212> TYPE: DNA

-continued

<213> ORGANISM: Artificial Sequence
<220> FEATURE:
<223> OTHER INFORMATION: primer for sequence number 10

<400> SEQUENCE: 25
cccaagctta cattttttcca tctctaa                                    27

<210> SEQ ID NO 26
<211> LENGTH: 26
<212> TYPE: DNA
<213> ORGANISM: Artificial Sequence
<220> FEATURE:
<223> OTHER INFORMATION: primer for sequence number 11

<400> SEQUENCE: 26
cgggatccag tgtcagtaga acagag                                      26

<210> SEQ ID NO 27
<211> LENGTH: 27
<212> TYPE: DNA
<213> ORGANISM: Artificial Sequence
<220> FEATURE:
<223> OTHER INFORMATION: primer for sequence number 11

<400> SEQUENCE: 27
cccaagctta cattttttcca tctctaa                                    27

<210> SEQ ID NO 28
<211> LENGTH: 28
<212> TYPE: DNA
<213> ORGANISM: Artificial Sequence
<220> FEATURE:
<223> OTHER INFORMATION: primer for sequence number 12

<400> SEQUENCE: 28
taacaaattg gatctatcgc ccgcggac                                    28

<210> SEQ ID NO 29
<211> LENGTH: 27
<212> TYPE: DNA
<213> ORGANISM: Artificial Sequence
<220> FEATURE:
<223> OTHER INFORMATION: primer for sequence number 12

<400> SEQUENCE: 29 ctttacccctt tctggtttct gttcttc                                    27

<210> SEQ ID NO 30
<211> LENGTH: 25
<212> TYPE: DNA
<213> ORGANISM: Artificial Sequence
<220> FEATURE:
<223> OTHER INFORMATION: primer for sequence number 13

<400> SEQUENCE: 30
cgggatccac agagggtgcc atcga                                       25

<210> SEQ ID NO 31
<211> LENGTH: 24
<212> TYPE: DNA
<213> ORGANISM: Artificial Sequence
<220> FEATURE:
<223> OTHER INFORMATION: primer for sequence number 13

<400> SEQUENCE: 31
ggaattccct ttctggtttc tgtt                                        24

<210> SEQ ID NO 32
<211> LENGTH: 26
<212> TYPE: DNA
<213> ORGANISM: Artificial Sequence
<220> FEATURE:
<223> OTHER INFORMATION: primer for sequence number 14

<400> SEQUENCE: 32
cgggatccat gattatctac cgggac                                         26

<210> SEQ ID NO 33
<211> LENGTH: 24
<212> TYPE: DNA
<213> ORGANISM: Artificial Sequence
<220> FEATURE:
<223> OTHER INFORMATION: primer for sequence number 14

<400> SEQUENCE: 33
ggaattctct actgaccatc ttgc                                           24

<210> SEQ ID NO 34
<211> LENGTH: 26
<212> TYPE: DNA
<213> ORGANISM: Artificial Sequence
<220> FEATURE:
<223> OTHER INFORMATION: primer for sequence number 15

<400> SEQUENCE: 34
cgggatccgt aaagcctttt atgact                                         26

<210> SEQ ID NO 35
<211> LENGTH: 27
<212> TYPE: DNA
<213> ORGANISM: Artificial Sequence
<220> FEATURE:
<223> OTHER INFORMATION: primer for sequence number 15

<400> SEQUENCE: 35
cccaagctta cattttttcca tctctaa                                       27

<210> SEQ ID NO 36
<211> LENGTH: 26
<212> TYPE: DNA
<213> ORGANISM: Artificial Sequence
<220> FEATURE:
<223> OTHER INFORMATION: primer for sequence number 16

<400> SEQUENCE: 36
cgggatccac aaaagaggcc tacaaa                                         26

<210> SEQ ID NO 37
<211> LENGTH: 26
<212> TYPE: DNA
<213> ORGANISM: Artificial Sequence
<220> FEATURE:
<223> OTHER INFORMATION: primer for sequence number 16

<400> SEQUENCE: 37
cgggatcctg gtttctgttc ttcaag                                         26

<210> SEQ ID NO 38
<211> LENGTH: 298
<212> TYPE: DNA
<213> ORGANISM: Artificial Sequence
<220> FEATURE:

```
<223> OTHER INFORMATION: Multiple Cloning Site of pRSET A

<400> SEQUENCE: 38
aatacgactc actataggga gaccacaacg gtttccctct agaaataatt ttgtttaact      60
ttaagaagga gatatacata tgcggggttc tcatcatcat catcatcatg gtatggctag    120
catgactggt ggacagcaaa tgggtcggga tctgtacgac gatgacgata aggatcgatg    180
gggatccgag ctcgagatct gcagctggta ccatggaatt cgaagcttga tccggctgct    240
aacaaagccc gaaaggaagc tgagttggct gctgccaccg ctgagcaata actagcat      298

<210> SEQ ID NO 39
<211> LENGTH: 71
<212> TYPE: PRT
<213> ORGANISM: Artificial Sequence
<220> FEATURE:
<223> OTHER INFORMATION: Multiple Cloning Site of pRSET A

<400> SEQUENCE: 39

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Glu Leu Glu Ile Cys Ser Trp Tyr His Gly Ile Arg
        35                  40                  45

Ser Leu Ile Arg Leu Leu Thr Lys Pro Glu Arg Lys Leu Ser Trp Leu
    50                  55                  60

Leu Pro Pro Leu Ser Asn Asn
65                  70

<210> SEQ ID NO 40
<211> LENGTH: 7
<212> TYPE: PRT
<213> ORGANISM: Artificial Sequence
<220> FEATURE:
<223> OTHER INFORMATION: HRF binding peptide

<400> SEQUENCE: 40

Trp Tyr Val Tyr Pro Ser Met
1               5
```